United States Patent
Portnoy et al.

(10) Patent No.: US 10,155,014 B2
(45) Date of Patent: *Dec. 18, 2018

(54) CYCLIC DI-AMP INDUCTION OF TYPE I INTERFERON

(71) Applicant: The Regents of the University of California, Oakland, CA (US)

(72) Inventors: Daniel A. Portnoy, Albany, CA (US); Joshua J. Woodward, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 33 days.

This patent is subject to a terminal disclaimer.

(21) Appl. No.: 15/682,201

(22) Filed: Aug. 21, 2017

(65) Prior Publication Data

US 2017/0360847 A1   Dec. 21, 2017

Related U.S. Application Data

(63) Continuation of application No. 14/737,112, filed on Jun. 11, 2015, now Pat. No. 9,763,987, which is a continuation of application No. 13/327,514, filed on Dec. 15, 2011, now Pat. No. 9,061,048.

(60) Provisional application No. 61/423,497, filed on Dec. 15, 2010.

(51) Int. Cl.
| | |
|---|---|
| A61K 35/74 | (2015.01) |
| C12N 15/63 | (2006.01) |
| A61K 35/15 | (2015.01) |
| A61K 39/00 | (2006.01) |
| A61K 39/29 | (2006.01) |
| A61K 35/00 | (2006.01) |

(52) U.S. Cl.
CPC ............. *A61K 35/74* (2013.01); *A61K 35/15* (2013.01); *A61K 39/0008* (2013.01); *A61K 39/0011* (2013.01); *A61K 39/29* (2013.01); *C12N 15/63* (2013.01); *A61K 2035/11* (2013.01); *A61K 2039/523* (2013.01); *C12N 2501/01* (2013.01)

(58) Field of Classification Search
None
See application file for complete search history.

(56) References Cited

U.S. PATENT DOCUMENTS

| | | | |
|---|---|---|---|
| 4,816,253 A * | 3/1989 | Likhite | A61K 39/0011 424/197.11 |
| 8,277,797 B2 | 10/2012 | Portnoy et al. | |
| 8,679,476 B2 | 3/2014 | Portnoy et al. | |
| 9,066,900 B2 | 6/2015 | Portnoy et al. | |
| 2004/0013690 A1 | 1/2004 | Portnoy et al. | |
| 2005/0249748 A1 | 11/2005 | Dubensky, Jr. et al. | |
| 2008/0286296 A1 * | 11/2008 | Ebensen | A61K 31/7084 424/194.1 |
| 2010/0285067 A1 | 11/2010 | Portnoy et al. | |

FOREIGN PATENT DOCUMENTS

WO    WO2008/066774    *    6/2008

OTHER PUBLICATIONS

Calvez et al. Folia Microbiol. 53 (5), 417-422 (2008).*
Feneck. Contin Educ Anaesth Crit Care Pain. 2007 7(6): 203-207.*
Woodward et al. Science. vol. 328:1703-1705 May 27, 2010 including supporting online material (15 pages).*
c-di-AMP retrieved Dec. 28, 2012 from http://invivogen.com/PDF/c_di_AMP_TDS.pdf.*
McWhirtier et al. "A host type I interferon response is induced by cytosolic snesing of the the bacterial second messenger cyclic-di-GMP", JEM (2009) vol. 206, No. 9, pp. 1899-1911.

* cited by examiner

*Primary Examiner* — Oluwatosin A Ogunbiyi
(74) *Attorney, Agent, or Firm* — Otto C. Guedelhoefer, IV; Bret E. Field; Bozicevic, Field & Francis LLP

(57) ABSTRACT

Methods of modulating type-I interferon production in a cell are provided. Aspects of the methods include modulating cytosolic cyclic di-adenosine monophosphate (c-di-AMP) activity in the cell in a manner sufficient to modulate type-I interferon production in the cell. Additional aspects of the invention include c-di-AMP activity modulatory compositions, e.g., c-di-AMP, mutant *Listeria* bacteria, cyclase and/or phosphodiesterase nucleic acid or protein compositions, etc. The subject methods and compositions find use in a variety of applications, including therapeutic applications.

20 Claims, 9 Drawing Sheets
Specification includes a Sequence Listing.

SEQUENCE LISTING

```
<160> NUMBER OF SEQ ID NOS: 15

<210> SEQ ID NO 1
<211> LENGTH: 37
<212> TYPE: DNA
<213> ORGANISM: Artificial Sequence
<220> FEATURE:
<223> OTHER INFORMATION: Synthetic Primer

<400> SEQUENCE: 1
gaggagcata tgaatatgaa agcagcaagt acatcag                37

<210> SEQ ID NO 2
<211> LENGTH: 38
<212> TYPE: DNA
<213> ORGANISM: Artificial Sequence
<220> FEATURE:
<223> OTHER INFORMATION: Synthetic Primer

<400> SEQUENCE: 2
gaggagctcg agtgcttttt ccgttttagt aacaattg               38

<210> SEQ ID NO 3
<211> LENGTH: 38
<212> TYPE: DNA
<213> ORGANISM: Artificial Sequence
<220> FEATURE:
<223> OTHER INFORMATION: Synthetic Primer

<400> SEQUENCE: 3
gaggagcggc cgatgaatat gaaagcagca agtacatc               38

<210> SEQ ID NO 4
<211> LENGTH: 31
<212> TYPE: DNA
<213> ORGANISM: Artificial Sequence
<220> FEATURE:
<223> OTHER INFORMATION: Synthetic Primer

<400> SEQUENCE: 4
gaggaggtcg actcagtggt ggtggtggtg g                      31

<210> SEQ ID NO 5
<211> LENGTH: 37
```

```
<212> TYPE: DNA
<213> ORGANISM: Artificial Sequence
<220> FEATURE:
<223> OTHER INFORMATION: Synthetic Primer

<400> SEQUENCE: 5
ccatgctgat tgctggggca atggtacaag caattgg                              37

<210> SEQ ID NO 6
<211> LENGTH: 37
<212> TYPE: DNA
<213> ORGANISM: Artificial Sequence
<220> FEATURE:
<223> OTHER INFORMATION: Synthetic Primer

<400> SEQUENCE: 6
ccaattgctt gtaccattgc cccagcaatc agcatgg                              37

<210> SEQ ID NO 7
<211> LENGTH: 36
<212> TYPE: DNA
<213> ORGANISM: Artificial Sequence
<220> FEATURE:
<223> OTHER INFORMATION: Synthetic Primer

<400> SEQUENCE: 7
gaactttgcc ccagcaattt gcccgacact ttcagg                               36

<210> SEQ ID NO 8
<211> LENGTH: 36
<212> TYPE: DNA
<213> ORGANISM: Artificial Sequence
<220> FEATURE:
<223> OTHER INFORMATION: Synthetic Primer

<400> SEQUENCE: 8
cctgaaagtg tcgggcaaat tgctggggca aagttc                               36

<210> SEQ ID NO 9
<211> LENGTH: 39
<212> TYPE: DNA
<213> ORGANISM: Artificial Sequence
<220> FEATURE:
<223> OTHER INFORMATION: Synthetic Primer

<400> SEQUENCE: 9
gaggagcggc cgatggattt ttccaatatg tcgatattg                            39

<210> SEQ ID NO 10
<211> LENGTH: 38
<212> TYPE: DNA
<213> ORGANISM: Artificial Sequence
<220> FEATURE:
<223> OTHER INFORMATION: Synthetic Primer

<400> SEQUENCE: 10
gaggaggtcg acatttaaaa ttcgatccat cattcgct                             38

<210> SEQ ID NO 11
<211> LENGTH: 273
<212> TYPE: PRT
<213> ORGANISM: Listeria monocytogenes

<400> SEQUENCE: 11

Met Asp Phe Ser Asn Met Ser Ile Leu His Tyr Leu Ala Asn Ile Val
 1               5                  10                  15
```

```
Asp Ile Leu Val Val Trp Phe Val Ile Tyr Lys Val Ile Met Leu Ile
            20                  25                  30
Arg Gly Thr Lys Ala Val Gln Leu Leu Lys Gly Ile Phe Ile Ile Ile
        35                  40                  45
Ala Val Lys Leu Leu Ser Gly Phe Phe Gly Leu Gln Thr Val Glu Trp
50                  55                  60
Ile Thr Asp Gln Met Leu Thr Trp Gly Phe Leu Ala Ile Ile Ile Ile
65                  70                  75                  80
Phe Gln Pro Glu Leu Arg Arg Ala Leu Glu Thr Leu Gly Arg Gly Asn
                85                  90                  95
Ile Phe Thr Arg Tyr Gly Ser Arg Ile Glu Arg Glu Gln His His Leu
            100                 105                 110
Ile Glu Ser Ile Glu Lys Ser Thr Gln Tyr Met Ala Lys Arg Arg Ile
        115                 120                 125
Gly Ala Leu Ile Ser Val Ala Arg Asp Thr Gly Met Asp Asp Tyr Ile
130                 135                 140
Glu Thr Gly Ile Pro Leu Asn Ala Lys Ile Ser Ser Gln Leu Leu Ile
145                 150                 155                 160
Asn Ile Phe Ile Pro Asn Thr Pro Leu His Asp Gly Ala Val Ile Ile
                165                 170                 175
Lys Gly Asn Glu Ile Ala Ser Ala Ala Ser Tyr Leu Pro Leu Ser Asp
            180                 185                 190
Ser Pro Phe Leu Ser Lys Glu Leu Gly Thr Arg His Arg Ala Ala Leu
        195                 200                 205
Gly Ile Ser Glu Val Thr Asp Ser Ile Thr Ile Val Val Ser Glu Glu
210                 215                 220
Thr Gly Gly Ile Ser Leu Thr Lys Gly Gly Glu Leu Phe Arg Asp Val
225                 230                 235                 240
Ser Glu Glu Glu Leu His Lys Ile Leu Leu Lys Glu Leu Val Thr Val
                245                 250                 255
Thr Ala Lys Lys Pro Ser Ile Phe Ser Lys Trp Lys Gly Gly Lys Ser
            260                 265                 270
Glu

<210> SEQ ID NO 12
<211> LENGTH: 822
<212> TYPE: DNA
<213> ORGANISM: Listeria monocytogenes

<400> SEQUENCE: 12
atggattttt ccaatatgtc gatattgcat tatctagcaa atattgtaga tattcttgtc     60
gtatggtttg taatttataa agtgatcatg ttaatccgag gtacaaaagc agtacaatta    120
ctaaaaggca tttttattat cattgcagtc aaactattaa gcggattttt tggtctccaa    180
acagtagaat ggattacgga tcagatgctt acttggggat ccttgcaat  tataattatc    240 ttccaaccgg aattacgccg tgctttagaa acgcttggac gaggtaatat tttttactcgt    300 tatggatcaa gaattgagcg tgaacagcat catttaatcg agtctatcga aaaatccacc    360
caatatatgg caaaacgtcg aattggggca ctgatttcag tggcacgcga tacaggcatg    420
gacgattata ttgaaacagg tattccgtta aatgcaaaaa tttcttctca attattaatt    480
aatattttta ttccgaatac accgcttcat gatggagcag ttattattaa aggaaacgaa    540
attgcatcgg cagcaagtta cttgccactt tcagatagcc cgttcttatc caaagaactt    600
```

```
ggaacgcgtc accgggctgc acttgggatt agtgaagtga cagatagtat tacgattgta    660
gtttctgaag agactggcgg aatttcccta actaaaggtg gagaactttt ccgtgatgtg    720
tcagaagaag agttacataa aattcttctt aagaactag tcacagtaac tgcaaagaaa     780
ccttctatct tttctaaatg gaaaggaggc aaaagcgaat ga                       822
```

<210> SEQ ID NO 13
<211> LENGTH: 350
<212> TYPE: PRT
<213> ORGANISM: Thermotoga maritime

<400> SEQUENCE: 13

```
Met Gly Val Lys Ser Leu Val Pro Gln Glu Leu Ile Glu Lys Ile Lys
  1               5                  10                  15

Leu Ile Ser Pro Gly Thr Glu Leu Arg Lys Ala Leu Asp Asp Ile Ile
             20                  25                  30

Asn Ala Asn Phe Gly Ala Leu Ile Phe Leu Val Asp Asp Pro Lys Lys
         35                  40                  45

Tyr Glu Asp Val Ile Gln Gly Gly Phe Trp Leu Asp Thr Asp Phe Ser
     50                  55                  60

Ala Glu Lys Leu Tyr Glu Leu Ser Lys Met Asp Gly Ala Ile Val Leu
 65                  70                  75                  80

Ser Glu Asp Ile Thr Lys Ile Tyr Tyr Ala Asn Val His Leu Val Pro
                 85                  90                  95

Asp Pro Thr Ile Pro Thr Gly Glu Thr Gly Thr Arg His Arg Thr Ala
            100                 105                 110

Glu Arg Leu Ala Lys Gln Thr Gly Lys Val Val Ile Ala Val Ser Arg
        115                 120                 125

Arg Arg Asn Ile Ile Ser Leu Tyr Tyr Lys Asn Tyr Lys Tyr Val Val
    130                 135                 140

Asn Gln Val Asp Phe Leu Ile Ser Lys Val Thr Gln Ala Ile Ser Thr
145                 150                 155                 160

Leu Glu Lys Tyr Lys Asp Asn Phe Asn Lys Leu Leu Ser Glu Leu Glu
                165                 170                 175

Val Leu Glu Leu Glu Asn Arg Val Thr Leu Ala Asp Val Val Arg Thr
            180                 185                 190

Leu Ala Lys Gly Phe Glu Leu Leu Arg Ile Val Glu Glu Ile Arg Pro
        195                 200                 205

Tyr Ile Val Glu Leu Gly Glu Glu Gly Arg Leu Ala Arg Met Gln Leu
    210                 215                 220

Arg Glu Leu Thr Glu Asp Val Asp Asp Leu Leu Val Leu Leu Ile Met
225                 230                 235                 240

Asp Tyr Ser Ser Glu Glu Val Glu Glu Glu Thr Ala Gln Asn Ile Leu
                245                 250                 255

Gln Asp Phe Ile Thr Arg Arg Glu Pro Ser Pro Ile Ser Ile Ser Arg
            260                 265                 270

Val Leu Gly Tyr Asp Val Gln Gln Ala Ala Gln Leu Asp Asp Val Leu
        275                 280                 285

Val Ser Ala Arg Gly Tyr Arg Leu Leu Lys Thr Val Ala Arg Ile Pro
    290                 295                 300

Leu Ser Ile Gly Tyr Asn Val Val Arg Met Phe Lys Thr Leu Asp Gln
305                 310                 315                 320

Ile Ser Lys Ala Ser Val Glu Asp Leu Lys Lys Val Glu Gly Ile Gly
                325                 330                 335
```

Glu Lys Arg Ala Arg Ala Ile Ser Glu Ser Ile Ser Ser Leu
                340                 345                 350

<210> SEQ ID NO 14
<211> LENGTH: 657
<212> TYPE: PRT
<213> ORGANISM: Listeria monocytogenes

<400> SEQUENCE: 14

Met Ser Gly Tyr Phe Gln Lys Arg Met Leu Lys Tyr Pro Leu Tyr Gly
 1               5                  10                  15

Leu Ile Ala Ala Thr Ile Ile Leu Ser Val Ile Thr Phe Phe Phe Ser
                20                  25                  30

Trp Trp Leu Ser Ala Leu Val Val Gly Ile Ile Leu Thr Val
            35                  40                  45

Ala Met Phe Tyr Phe Glu Tyr Arg Leu Asn Glu Asp Val Gln Leu Tyr
        50                  55                  60

Val Ser Asn Leu Thr Tyr Arg Ile Lys Arg Ser Glu Glu Ala Leu
 65                  70                  75                  80

Val Glu Met Pro Met Gly Ile Leu Leu Tyr Asp Glu His Tyr Lys Ile
                85                  90                  95

Glu Trp Val Asn Pro Phe Met Ser Lys Tyr Phe Asp Lys Ala Glu Leu
            100                 105                 110

Ile Gly Glu Ser Leu Glu Val Gly Pro Glu Phe Leu Asp Val Ile
        115                 120                 125

Thr Gly Asn Asp Glu Lys Gly Ile Met Ser Ile Ala Trp Arg Asp His
130                 135                 140

Arg Phe Asp Thr Ile Val Lys Arg Lys Glu Arg Ile Leu Tyr Leu Tyr
145                 150                 155                 160

Asp Arg Thr Glu Tyr Tyr Asp Leu Asn Lys Lys Phe Gln Ala Asn Lys
                165                 170                 175

Ser Val Phe Ala Val Ile Phe Leu Asp Asn Tyr Asp Glu Trp Ala Gln
            180                 185                 190

Gly Met Asp Asp Arg Arg Arg Ser Ala Leu Asn Asn Leu Val Thr Ser
        195                 200                 205

Met Leu Thr Asn Trp Ala Arg Glu His Arg Ile Tyr Leu Lys Arg Ile
210                 215                 220

Ser Thr Asp Arg Phe Met Ala Phe Leu Thr Glu Glu Met Leu Lys Arg
225                 230                 235                 240

Leu Glu Glu Glu Lys Phe Gln Ile Leu Asp Arg Ile Arg Glu Arg Thr
                245                 250                 255

Ser Lys Gln Asn Ile Pro Leu Thr Leu Ser Ile Gly Ile Gly Tyr Lys
            260                 265                 270

Glu Asp Asp Leu Ile Gln Leu Ala Asp Leu Ala Gln Ser Ser Leu Asp
        275                 280                 285

Leu Ala Leu Gly Arg Gly Gly Asp Gln Val Val Ile Lys Gln Pro Glu
290                 295                 300

Gly Lys Val Arg Phe Tyr Gly Gly Lys Thr Asn Pro Met Glu Lys Arg
305                 310                 315                 320

Thr Arg Val Arg Ala Arg Val Ile Ser Gln Ala Leu Gln Glu Leu Ile
                325                 330                 335

Thr Gln Ser Asp Gln Val Phe Val Met Gly His Arg Tyr Pro Asp Met
            340                 345                 350

Asp Val Ile Gly Ser Ser Leu Gly Val Met Arg Ile Ala Glu Met Asn
        355                 360                 365

Asp Arg Asn Ala Tyr Val Val Glu Pro Gly Lys Met Ser Pro Asp
    370                 375                 380

Val Lys Arg Leu Met Asn Glu Ile Glu Glu Tyr Pro Asn Val Ile Lys
385                 390                 395                 400

Asn Ile Val Thr Pro Gln Val Ala Leu Glu Asn Ile Thr Glu Lys Ser
                405                 410                 415

Leu Leu Val Val Val Asp Thr His Lys Pro Ser Met Val Ile Asn Lys
            420                 425                 430

Glu Leu Leu Asp Ser Ala Thr Asn Val Val Val Asp His His Arg
        435                 440                 445

Arg Ser Glu Glu Phe Val Gly Ser Pro Val Leu Val Tyr Ile Glu Pro
    450                 455                 460

Tyr Ala Ser Ser Thr Ala Glu Leu Ile Thr Glu Leu Phe Glu Tyr Gln
465                 470                 475                 480

Pro Asp Leu Glu Gln Val Gly Lys Ile Glu Ala Thr Ala Leu Leu Ser
                485                 490                 495

Gly Ile Val Val Asp Thr Lys Asn Phe Thr Leu Arg Thr Gly Ser Arg
            500                 505                 510

Thr Phe Asp Ala Ala Ser Tyr Leu Arg Ser Leu Gly Ala Asp Thr Ile
        515                 520                 525

Leu Val Gln Gln Phe Leu Lys Glu Asp Ile Thr Thr Phe Thr Gln Arg
    530                 535                 540

Ser Arg Leu Val Glu Ser Leu Glu Ile Tyr His Asp Gly Met Ala Ile
545                 550                 555                 560

Ala Thr Gly His Glu Asp Glu Glu Phe Gly Thr Val Ile Ala Ala Gln
                565                 570                 575

Ala Ala Asp Thr Met Leu Ser Met Glu Gly Val Gln Ala Ser Phe Val
            580                 585                 590

Ile Thr Leu Arg Pro Asp Lys Leu Ile Gly Ile Ser Ala Arg Ser Leu
        595                 600                 605

Gly Gln Ile Asn Val Gln Val Ile Met Glu Lys Leu Gly Gly Gly Gly
    610                 615                 620

His Leu Ser Asn Ala Ala Thr Gln Leu Lys Asp Val Thr Ile Ala Glu
625                 630                 635                 640

Ala Glu Lys Gln Leu Ile Ser Ala Ile Asp Ala Tyr Trp Lys Gly Glu
                645                 650                 655

Thr

<210> SEQ ID NO 15
<211> LENGTH: 1974
<212> TYPE: DNA
<213> ORGANISM: Listeria monocytogenes

<400> SEQUENCE: 15
atgtcaggct attttcaaaa acgaatgctt aaatatccat tatacggtct gattgcagcg    60
acaattattt tgagcgtaat cacgttcttt ttttcgtggt ggttatcggc gttagttgtt   120
gttggcggaa ttattcttac ggttgcgatg ttttattttg aatatcgctt gaatgaagat   180
gtgcaactat atgtttctaa tttaacgtat cggattaagc gtagtgaaga agaagcgctt   240
gttgaaatgc cgatgggaat actgctgtat gatgaacatt acaaaatcga atgggttaac   300
ccgtttatgt caaatactt tgataaggca gagttaatcg gggaatcttt ggaagaagta   360
ggaccggaat ttttgacgt tattactggg aatgatgaaa aggggattat gtcgattgct   420

-continued

```
tggcgtgatc accgttttga tacgatagta aagcgtaagg aacgaattt atatttatat      480
gatcgcacag aatattatga tttaaacaag aaatttcaag cgaataaatc tgtatttgcg      540
gttatttct tagataatta tgatgaatgg gcgcagggca tggatgatag acgtcgcagt       600
gctttaaata atttggtgac gtcgatgttg accaactggg ctagggaaca tcgtatttat      660
ttgaaacgga tttcgacaga ccgatttatg gccttttga cggaggaaat gttgaagcgg       720
ttggaggaag agaagtttca aatattggac cggattcgcg aacggacgtc gaagcaaaat      780
attcctttaa cgcttagtat tgggattggt tataaggaag atgatttgat tcagctggcc      840
gatttggcgc agtctagtct agatcttgct ttagggcgcg gcggcgatca ggttgtaatt      900
aagcaacctg aaggaaaagt gcgttttat ggtgggaaaa caaatccgat ggaaaaacgg       960
actcgtgttc gcgcgcgtgt gatttcgcaa gcattgcaag agctgattac gcaaagtgac     1020
caagtttttg ttatgggca ccgctatccg gatatggacg taattggttc gagtcttgga      1080
gtgatgcgga ttgctgagat gaatgatcgg aatgcttatg tggttgtgga acctggcaaa     1140
atgagtccag atgtgaagcg actaatgaat gaaattgaag aatatccgaa tgtaattaaa     1200
aatattgtta caccgcaagt cgcactggaa aatatcacgg agaagagttt gctcgttgtt     1260
gttgatacac acaaaccttc gatggttatt aataaggaat tgctggactc agctacgaat     1320
gtggttgttg tcgatcatca ccgtcgttca gaggaatttg ttgggagtcc ggttcttgtt     1380
tatatcgagc catatgcgtc atctactgcc gaattgatta cggagctatt tgagtatcaa     1440
ccggatttag agcaggttgg gaaaatcgag gcaacggcgc ttctttccgg gattgtggtt     1500
gatacgaaga actttacgct gcggactggg tcgcgaacgt ttgatgcggc aagttattta     1560
cggtcgcttg gtgcggacac gattttggtg cagcaattt tgaaagaaga tattactact     1620
tttacacagc ggagtcgttt agtggagtcg cttgaaattt atcatgatgg tatggcgatt     1680
gcgactggac atgaggacga ggaatttggc acagttatag ctgcgcaggc ggcagatacg     1740
atgctttcga tggaaggcgt gcaggcatcc tttgttatta cgctacgtcc ggataaatta     1800
atcgggatta gcgcgagatc gcttggccaa atcaatgtgc aagtcattat ggaaaaacta     1860
ggcggtggcg gacatttatc gaatgcagcc acacagctta aagatgttac aattgcagaa     1920
gcagaaaaac aattaattag cgccattgat gcgtattgga agggagaaac ataa           1974
```

CYCLIC DI-AMP INDUCTION OF TYPE I INTERFERON

RELATED APPLICATIONS

This application is a continuation of U.S. patent application Ser. No. 14/737,112 filed on Jun. 11, 2015, which application is a continuation of U.S. patent application Ser. No. 13/327,514 filed on Dec. 15, 2011, now U.S. Pat. No. 9,061,048, which application, pursuant to 35 U.S.C. § 119 (e), claims priority to U.S. Provisional Patent Application No. 61/423,497 filed on Dec. 15, 2010; the disclosures of which are herein incorporated by reference in their entirety.

GOVERNMENT RIGHTS

This invention was made with Government support under grant numbers A1063302, CA009179 and A1027655 awarded by the National Institutes of Health. The Government has certain rights in the invention.

BACKGROUND OF THE INVENTION

Interferons (also referred to as "IFN" or "IFNs") are proteins having a variety of biological activities, some of which are antiviral, immunomodulating and antiproliferative. They are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. In most cases, interferons provide better protection to tissues and cells of the kind from which they have been produced than to other types of tissues and cells, indicating that human-derived interferon could be more efficacious in treating human diseases than interferons from other species. Interferons may be classified as Type-I, Type-II and Type-III interferons. Mammalian Type-I interferons include IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin). Interferons have potential in the treatment of a large number of human cancers since these molecules have anticancer activity which acts at multiple levels. First, interferon proteins can directly inhibit the proliferation of human tumor cells. The antiproliferative activity is also synergistic with a variety of approved chemotherapeutic agents such as cisplatin, 5FU and paclitaxel. Secondly, the immunomodulatory activity of interferon proteins can lead to the induction of an anti-tumor immune response. This response includes activation of NK cells, stimulation of macrophage activity and induction of MHC class I surface expression leading to the induction of anti-tumor cytotoxic T lymphocyte activity. In addition, interferons play a role in cross-presentation of antigens in the immune system. Moreover, some studies further indicate that IFN-β protein may have anti-angiogenic activity. Angiogenesis, new blood vessel formation, is critical for the growth of solid tumors. Evidence indicates that IFN-β may inhibit angiogenesis by inhibiting the expression of pro-angiogenic factors such as bFGF and VEGF. Lastly, interferon proteins may inhibit tumor invasiveness by affecting the expression of enzymes such as collagenase and elastase which are important in tissue remodeling.

Interferons also appear to have antiviral activities that are based on two different mechanisms. For instance, type I interferon proteins (α and β) can directly inhibit the replication of human hepatitis B virus ("HBV") and hepatitis C virus ("HCV"), but can also stimulate an immune response which attacks cells infected with these viruses.

The method of administering interferon is an important factor in the clinical application of this important therapeutic agent. Systemic administration of interferon protein by intravenous, intramuscular or subcutaneous injection has been most frequently used with some success in treating disorders such as hairy cell leukemia, Acquired Immune Deficiency Syndrome (AIDS) and related Kaposi's sarcoma. It is known, however, that proteins in their purified form are especially susceptible to degradation. In particular, for interferon-β, the primary mechanism(s) of interferon degradation in solution are aggregation and deamidation. The lack of interferon stability in solutions and other products has heretofore limited its utility. Therefore, a more effective method of modulating the level of interferons, such as interferon-β, is needed.

SUMMARY

Methods of modulating type-I interferon production in a cell are provided. Aspects of the methods include modulating cytosolic cyclic di-adenosine monophosphate (c-di-AMP) activity in the cell in a manner sufficient to modulate type-I interferon production in the cell. Additional aspects of the invention include c-di-AMP activity modulatory compositions, e.g., c-di-AMP, mutant Listeria bacteria, cyclase and/or phosphodiesterase nucleic acid or protein compositions, etc. The subject methods and compositions find use in a variety of applications, including therapeutic applications.

Methods of modulating type-I interferon production in a cell are provided. Aspects of the methods include modulating cytosolic cyclic di-adenosine monophosphate (c-di-AMP) activity in the cell in a manner sufficient to modulate type-I interferon production in the cell. Additional aspects of the invention include mutant Listeria bacteria having a mutation which modulates secretion of a compound selected from the group consisting of: c-di-AMP; cytosolic di-adenylate cyclase and c-di-AMP phosphodiesterase; as compared to its corresponding wild-type control. The subject methods and compositions find use in a variety of applications, including therapeutic applications.

Accordingly, aspects of the invention include methods of modulating type-I interferon production in a cell by modulating cytosolic cyclic di-adenosine monophosphate (c-di-AMP) activity in the cell in a manner sufficient to modulate type-I interferon production in the cell.

In some instances, the method is a method of enhancing type-I interferon production in a cell and the method comprises increasing cytosolic c-di-AMP activity in the cell. In some of these embodiments, the method comprises introducing c-di-AMP or a functional analogue thereof into the cell. In some of these embodiments, the method comprises introducing into the cell a bacterium that increases cytosolic c-di-AMP in the cell, e.g., a Listeria bacterium. The Listeria bacterium may be a mutant that secretes enhanced amounts of c-di-AMP as compared to its corresponding wild-type bacterium. The mutant may have enhanced di-adenylate cyclase activity as compared to its corresponding wild-type bacterium, e.g., the Listeria bacterium may comprise a lmo2120 mutation. The mutant may have reduced c-di-AMP phosphodiesterase activity as compared to its corresponding wild-type bacterium, e.g., the Listeria bacterium may include an lmo0052 mutation. In some instances, the bacterium secretes a di-adenylate cyclase into the cell, e.g., lmo2120 or a mutant thereof. In some embodiments, the method includes enhancing cytosolic di-adenylate cyclase activity in the cell, e.g., by decreasing c-di-AMP phosphodiesterase activity in the cell.

In some embodiments, the method is a method of decreasing type-I interferon production in a cell and the method comprises decreasing cytosolic c-di-AMP activity in the cell. Embodiments of such methods may include introducing c-di-AMP activity inhibitor into the cell. In some instances, the method may include introducing into the cell a bacterium that decreases cytosolic c-di-AMP in the cell. The bacterium may be a *Listeria* bacterium. In some instances, the bacterium secretes a c-di-AMP phosphodiesterase into the cell, e.g., lmo0052 or a mutant thereof. In some embodiments, the method comprises decreasing cytosolic di-adenylate cyclase activity in the cell and/or increasing c-di-AMP phosphodiesterase activity in the cell.

In certain methods of the invention, the cell is a macrophage. In methods of the invention, the type-I interferon may be interferon-β. The cell may be in vitro or in vivo, e.g., part of a multi-cellular organism, such as a mammal (e.g., human).

Methods of the invention may be methods of expression a heterologous protein in a subject. Methods of the invention may be methods of vaccinating a subject. Methods of the invention may be methods of treating a subject for a disease condition.

Aspects of the invention further include mutant *Listeria* bacterium comprising a mutation which modulates secretion of a compound selected from the group consisting of: c-di-AMP; cytosolic di-adenylate cyclase and c-di-AMP phosphodiesterase; as compared to its corresponding wild-type control. As such, the mutation may be a mutation that enhances secretion of c-di-AMP. In such embodiments, the mutation may enhance di-adenylate cyclase activity in the bacterium, e.g., where the mutation is a lmo2120 mutation. The mutation may decrease c-di-AMP phosphodiesterase activity in the cell, e.g., where the mutation is an lmo0052 mutation. The mutation may enhance secretion of cytosolic di-adenylate cyclase, e.g., where the mutation is a lmo2120 mutation. The mutation may enhance secretion of c-di-AMP phosphodiesterase, e.g., where the mutation is a lmo0052 mutation.

The *Listeria* bacterium may be *Listeria monocytogenes*. The *Listeria* bacterium may be attenuated. In some instances, the *Listeria* bacterium increases interferon-β production in macrophages as compared to its corresponding wild-type control. In some instances, the *Listeria* bacterium decreases interferon-β production in macrophages as compared to its corresponding wild-type control. The *Listeria* bacterium may include a heterologous nucleic acid, e.g., where the heterologous nucleic acid is integrated. The heterologous nucleic acid may encode at least one product, such as an antigen.

Aspects of the invention also include vaccines that include a mutant *Listeria* bacterium, e.g., as described above.

Aspects of the invention also include methods of eliciting or boosting a cellular immune response in a subject by administering to the subject an effective amount of a vaccine, e.g., as described above.

Aspects of the invention also include methods for modulating interferon-β production in a mammalian subject by administering to the mammalian subject an effective amount of a *Listeria* bacterium, e.g., as described above. In some instances, the mammalian subject has a neoplastic condition, e.g., cancer. In some instances, the mammalian subject has a viral infection, e.g., Hepatitis C viral infection. In some instances, the mammalian subject has multiple sclerosis.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
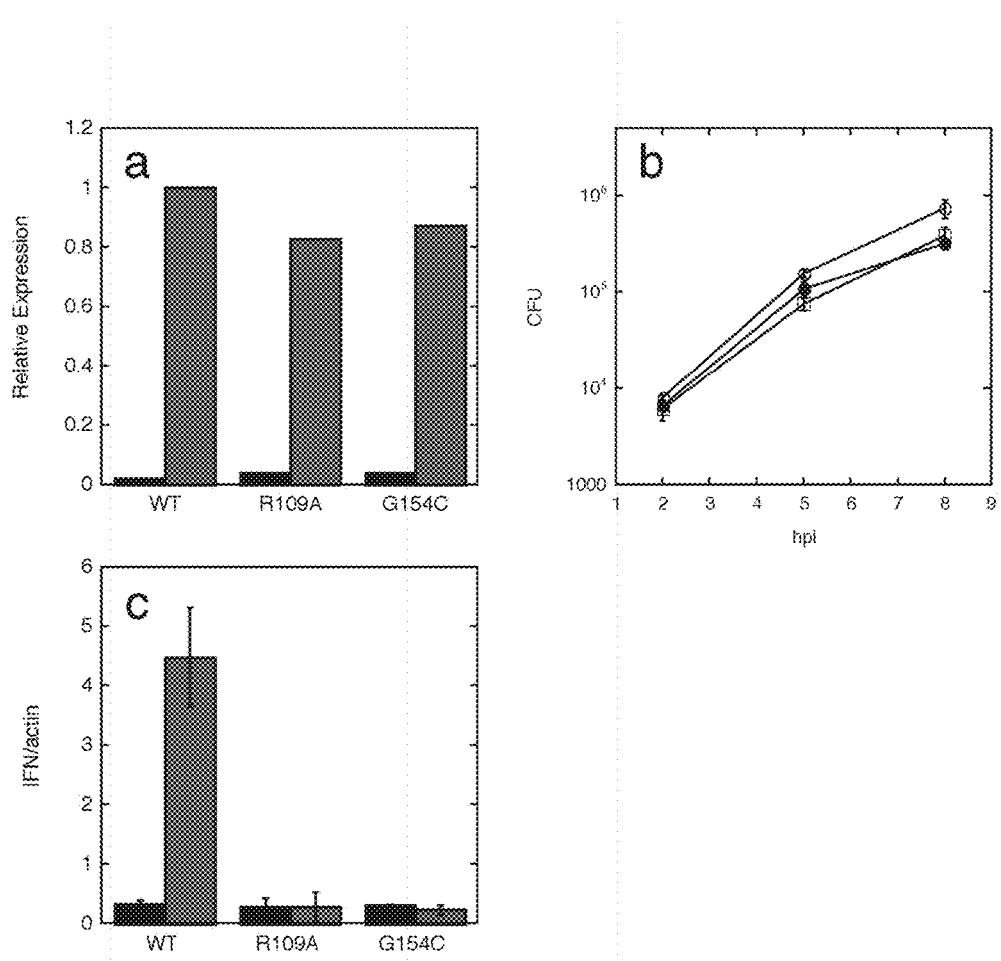
FIG. 1. MDR transport activity is necessary for IFN-β induction during infection. An IPTG inducible integration vector containing hexa-histidine tagged wild-type, R109A, or G154C mutant MdrM was integrated into the mdrM- strain. (a) Relative expression of $MdrM_{His6x}$ variants in *L. monocytogenes* membrane fractions in the absence (black bars) and presence (grey bars) of IPTG was quantified by western blot. (b) Intracellular growth of WT $MdrM_{His6x}$ (closed circles), R109A $MdrM_{His6x}$ (open circles), and G154C $MdrM_{His6x}$ (open squares) in bone marrow derived macrophages (BMMs) in the presence of IPTG. (c) qRT-PCR analysis of IFN-β induction by MdrM variants in the absence (black bars) and presence (grey bars) of IPTG during BMM infection.

Methods of modulating type-I interferon production in a cell are provided. Aspects of the methods include modulating cytosolic cyclic di-adenosine monophosphate (c-di-AMP) activity in the cell in a manner sufficient to modulate type-I interferon production in the cell. Additional aspects of the invention include c-di-AMP activity modulatory compositions. The subject methods and compositions find use in a variety of applications, including therapeutic applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be constructed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, methods of modulating type-I interferon production in a cell, e.g., in vitro or in vivo, where the target cell is a eukaryotic cell, are provided. By modulating type-I interferon production is meant that the subject methods change, e.g., enhance or inhibit, type-I interferon production in a cell, as compared to a control. The magnitude of the modulation may vary, and in some instances is 2-fold or greater, such as 5-fold or greater, including 10-fold or greater, as compared to a suitable control. As such, in some instances, the methods are methods of increasing type-I interferon production in a cell, e.g., by a magnitude of 2-fold or greater, such as 5-fold or greater, including 10-fold or greater, as compared to a suitable control. In yet other instances, the methods are methods of decreasing type-I interferon production in a cell, e.g., by a magnitude of 2-fold or greater, such as 5-fold or greater, including 10-fold or greater, as compared to a suitable control.

Aspects of the methods include modulating cytosolic cyclic di-adenosine monophosphate (c-di-AMP) activity in the cell in a manner sufficient to modulate type-I interferon production in the cell. Cytosolic cyclic di-adenosine monophosphate (c-di-AMP) activity refers to the amount of level of active c-di-AMP in a cell. By modulating c-di-AMP activity is meant that the subject methods change, e.g., enhance or inhibit, c-di-AMP activity in a cell, as compared to a control. The magnitude of the modulation may vary, and in some instances is 2-fold or greater, such as 5-fold or greater, including 10-fold or greater, as compared to a suitable control. As demonstrated in the Experimental Section below, the amount of active c-di-AMP in the cell is directly proportional to the level of type-I interferon production in the cell. As such, in some instances, the methods are methods of increasing c-di-AMP activity in a cell, e.g., as described below, such as 5-fold or greater, including 10-fold or greater, as compared to a suitable control. In yet other instances, the methods are methods of decreasing c-di-AMP activity in a cell, e.g., as described below, by a magnitude of 2-fold or greater, such as 5-fold or greater, including 10-fold or greater, as compared to a suitable control.

Modulation of cytosolic c-di-AMP activity may be accomplished using a variety of different approaches. In some instances, the method comprises contacting a target cell with a c-di-AMP activity modulatory agent, i.e., an agent that enhances or decreases c-di-AMP activity in the target cell. c-di-AMP activity modulatory agents may vary, and include but are not limited to: small molecules agents, bacterial agents, and nucleic acid/protein agents, etc.

Figure 3:
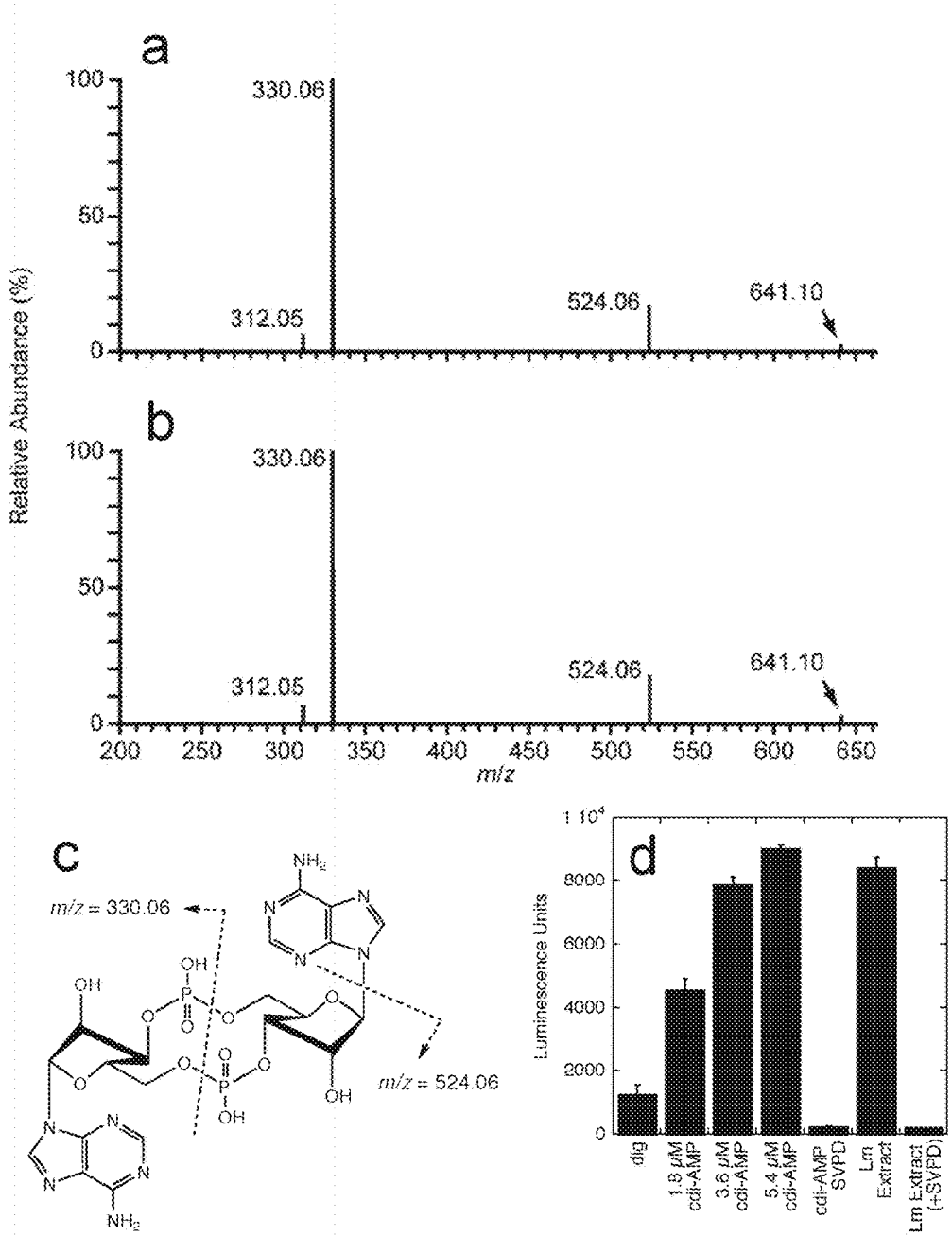
FIG. 3. Cyclic di-AMP is an IFN-β activating ligand. (a) Tandem mass spectrum resulting from collisionally activated dissociation of the singly charged positive ion at m/z=659.11 formed from an active fraction of *Listeria monocytogenes*. (b) Tandem mass spectrum of commercially obtained sample of purified c-di-AMP. The fragment ions at m/z=641.10 and 312.05 correspond to neutral losses of 18 Da from the precursor ion (m/z=659.11) and from the fragment ion at m/z=330.06, respectively, and are consistent with neutral loss of water molecules from these respective ions. Fragmentation pathways of c-di-AMP are shown in (c). (d) Commercial c-di-AMP standard (BioLog Life Sciences Institute, Denmark) was added to BMMs in increasing amount. IFN-β production by BMMs was detected using the type I IFN reporter cell line (ISRE L929). Commercial c-di-AMP standard and the active *L. monocytogenes* fraction were treated with snake venom phosphodiesterase (SVPD). Error bars represent standard deviation of single samples measured in triplicate.

In some instances, the c-di-AMP activity modulatory agent is c-di-AMP or a functional analogue thereof. c-di-AMP has the structure shown in FIG. 3c. Also of interest are functional analogues of c-di-AMP, e.g., 2'-bis(tert-butyldimethylsilyl)-c-di-AMP or as described below, where the functional analogues exhibit similar functional activity and may have a similar structure to c-di-AMP. In some instances, the functional analogue is not c-di-GMP. Of interest as functional analogues are small molecule agents. Naturally occurring or synthetic small molecule compounds of interest include numerous chemical classes, such organic molecules, including small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing suitable screening protocols. c-di-AMP and functional analogues finding use in embodiments of the invention (as well as methods of their administration) are further described in published United States Patent Application Publication No. US 2008/0286296 A1; the disclosure of which is herein incorporated by reference.

Also of interest as c-di-AMP activity modulatory agents are bacterial agents, e.g., a Listeria bacterial agents. Bacteria of interest include mutant bacteria, e.g., mutant Listeria bacteria, which include a mutation that modulates secretion of one or more compounds that ultimately modulate c-di-AMP activity in the target cell. Compounds of interest whose secretion may be modulated (as compared to a control) include compounds selected from the group consisting of: c-di-AMP; cytosolic di-adenylate cyclase and c-di-AMP phosphodiesterase and combinations thereof. One or more of these compounds may be modulated as compared to its corresponding wild-type control, as desired.

In some instances, the Listeria bacteria modulate interferon-$\beta$ production, e.g., in macrophages. The term "modulates" as used herein refers to an increase or a decrease, e.g., in secretion of c-di-AMP, in interferon-$\beta$ production, etc. In some embodiments, the modulation is an increase or decrease of at least about 10%, at least about 20%, at least about 30%, at least about 40%, at least about 50%, at least about 60%, at least about 70%, at least about 80%, at least about 90%, at least about 95%, or at least about 100% as compared to a Listeria bacteria that does not include the mutation, e.g., a corresponding wild type control.

In some embodiments, the mutant Listeria bacteria increase interferon-$\beta$ production as compared to Listeria bacteria that do not include the mutation, such as a wild-type Listeria bacterium. In such embodiments, the increase is from about 1.5-fold increase to about 50-fold increase or more, including about 2-fold increase to about 45-fold increase, about 5-fold increase to about 40-fold increase, about 10-fold increase to about 35-fold increase, about 15-fold increase to about 30-fold increase, about 20-fold increase to about 30-fold increase, and the like.

In other embodiments, the mutant Listeria bacteria decrease interferon-$\beta$ production as compared to Listeria bacteria that do not include the mutation. In such embodiments, the increase is from about 1.5-fold decrease to about 50-fold decrease or more, including about 2-fold decrease to about 45-fold decrease, about 5-fold decrease to about 40-fold decrease, about 10-fold decrease to about 35-fold decrease, about 15-fold decrease to about 30-fold decrease, about 20-fold decrease to about 30-fold decrease, and the like.

In certain embodiments, mutant species according to the subject invention, are ones that modulate (e.g., increase or decrease) interferon-$\beta$ production as compared to their corresponding wild-type strain in a macrophage cell culture. In this assay, macrophages are infected with test and reference, e.g., wild-type, strains of bacteria. Following a period of time, e.g., 4 to 18 hours, the macrophage culture media is collected and the amount of Type I interferon secreted by the macrophages is detected using a reporter gene such as luciferase cloned under regulation of a Type I interferon signaling pathway. The level of the reporter gene is then measured test and reference, e.g., wild-type, strains of bacteria to identify mutant *Listeria* strains that modulate (e.g., increase or decrease) interferon-β production.

The subject bacteria may be any species that includes a mutation according to the subject invention. Thus, strains of *Listeria* other than *L. monocytogenes* may be used for the generation of mutants according to the present invention. In certain embodiments, the *Listeria* strain is *L. monocytogenes*.

Specific mutant *Listeria* bacteria of interest include those that exhibit enhanced production and/or secretion of c-di-AMP by the bacteria, or that promote enhanced production or activity of c-di-AMP in the cell. Examples of such species include those in which the mutation enhances di-adenylate cyclase activity in the bacterium or the cell, e.g., a mutation that enhances the expression, secretion or activity of a polypeptide comprising a di-adenylate cyclase, or DAC, domain. By "DAC domain" it is meant a peptide domain that confers di-adenylate cyclase activity on a protein, for example, the DAC domain at residues 100-240 of the di-adenylate cyclase gene lmo2120 (also known as dacA or YbbP; e.g. *Listeria monocytogenes* lmo2120, the polypeptide sequence for which is (SEQ ID NO: 11)
MDFSNMSILHYLANIVDILVVWFVIYKVIMLIRGTKAVQLLKGIFIIIAV

KLLSGFFGLQTVEWITDQMLTWGFLAIIIIFQPELRRALETLGRGNIFTR

YGSRIEREQHHLIESIEKSTQYMAKRRIGALISVARDTGMDDYIETGIPL

NAKISSQLLINIFIPNTPLHDGAVIIKGNEIASAASYLPLSDSPFLSKEL

GTRHRAALGISEVTDSITIVVSEETGGISLTKGGELFRDVSEEELHKILL

KELVTVTAKKPSIFSKWKGGKSE, and the nucleic acid sequence for which is (SEQ ID NO: 12))
ATGGATTTTTCCAATATGTCGATATTGCATTATCTAGCAAATATTGTAGA

TATTCTTGTCGTATGGTTTGTAATTTATAAAGTGATCATGTTAATCCGAG

GTACAAAAGCAGTACAATTACTAAAAGGCATTTTTATTATCATTGCAGTC

AAACTATTAAGCGGATTTTTTGGTCTCCAAACAGTAGAATGGATTACGGA

TCAGATGCTTACTTGGGGATTCCTTGCAATTATAATTATCTTCCAACCGG

AATTACGCCGTGCTTTAGAAACGCTTGGACGAGGTAATATTTTTACTCGT

TATGGATCAAGAATTGAGCGTGAACAGCATCATTTAATCGAGTCTATCGA

AAAATCCACCCAATATATGGCAAAACGTCGAATTGGGGCACTGATTTCAG

TGGCACGCGATACAGGCATGGACGATTATATTGAAACAGGTATTCCGTTA

AATGCAAAAATTTCTTCTCAATTATTAATTAATATTTTTATTCCGAATAC

ACCGCTTCATGATGGAGCAGTTATTATTAAAGGAAACGAAATTGCATCGG

CAGCAAGTTACTTGCCACTTTCAGATAGCCCGTTCTTATCCAAAGAACTT

GGAACGCGTCACCGGGCTGCACTTGGGATTAGTGAAGTGACAGATAGTAT

TACGATTGTAGTTTCTGAAGAGACTGGCGGAATTTCCCTAACTAAAGGTG

GAGAACTTTTCCGTGATGTGTCAGAAGAAGAGTTACATAAAATTCTTCTT

AAAGAACTAGTCACAGTAACTGCAAAGAAACCTTCTATCTTTTCTAAATG

GAAAGGAGGCAAAAGCGAATGA;

or the DAC domain at residues 1-145 of DisA (e.g., *Thermotoga maritime* DisA, Witte et al. Mol. Cell 30:167-178, the polypeptide sequence for which is (SEQ ID NO: 13))
MGVKSLVPQELIEKIKLISPGTELRKALDDIINANFGALIFLVDDPKKYE

DVIQGGFWLDTDFSAEKLYELSKMDGAIVLSEDITKIYYANVHLVPDPTI

PTGETGTRHRTAERLAKQTGKVVIAVSRRRNIISLYYKNYKYVVNQVDFL

ISKVTQAISTLEKYKDNFNKLLSELEVLELENRVTLADVVRTLAKGFELL

RIVEEIRPYIVELGEEGRLARMQLRELTEDVDDLLVLLIMDYSSEEVEEE

TAQNILQDFITRREPSPISISRVLGYDVQQAAQLDDVLVSARGYRLLKTV

ARIPLSIGYNVVRMFKTLDQISKASVEDLKKVEGIGEKRARAISESISSL

KHRKTSE.

For example, the bacterial genome may be manipulated to overexpress the native di-adenylate cyclase gene lmo2120, or a mutant thereof, e.g. a fragment or mutant comprising di-adenylate cyclase activity, for example, by expressing multiple copies of the lmo2120 gene or di-adenylate cyclase active lmo2102 mutant or expressing the native dacA gene or di-adenylate cyclase active mutant under control of a strong, e.g., constitutive, promoter. By "native" and "native polypeptide" it is meant a polypeptide found in nature. By "mutant" or "variant" it is meant a mutant of the native polypeptide having less than 100% sequence identity with the native sequence. For example, variants include polypeptides having 60% sequence identity or more with a full length native protein having di-adenylate cyclase activity, e.g. dacA/lmo2120m, DisA, etc., e.g. 65%, 70%, 75%, or 80% or more identity, such as 85%, 90%, or 95% or more identity, for example, 98% or 99% identity with the full length native protein, where mutants of interest include deletion, insertion and substitution mutants. Variants also include fragments of a native polypeptide, where the variants maintain di-adenylate cyclase activity, e.g. the DAC domain of lmo2120, DisA, etc. e.g. a fragment comprising residues 100-240 of lmo2120 or the comparable sequence in a lmo2120 homolog or ortholog, or comprising residues 1-147 of DisA, or the comparable sequence in a DisA homolog or ortholog, as well as active mutants thereof. Examples of such species further include bacteria having additional active coding sequences of wild type or functional lmo2120, e.g., where the bacteria harbor one or more additional wild type sequences under the control of a constitutive or inducible promoter.

Other examples of mutant *Listeria* bacteria that exhibit enhanced production and/or secretion of c-di-AMP by the bacteria or that promote enhanced production or activity of c-di-AMP in the cell include bacteria that exhibit reduced cyclic nucleotide phosphodiesterase activity, i.e., reduced c-di-AMP phosphodiesterase activity, e.g., bacteria comprising a null or hypomorphic mutation in the *Listeria* gene lmo0052. The amino acid sequence of lmo0052 is:

(SEQ ID NO: 14)
MSGYFQKRMLKYPLYGLIAATIILSVITFFFSWWLSALVVVGGIILTVAM

FYFEYRLNEDVQLYVSNLTYRIKRSEEEALVEMPMGILLYDEHYKIEWVN

PFMSKYFDKAELIGESLEEVGPEFLDVITGNDEKGIMSIAWRDHRFDTIV

KRKERILYLYDRTEYYDLNKKFQANKSVFAVIFLDNYDEWAQGMDDRRRS

ALNNLVTSMLTNWAREHRIYLKRISTDRFMAFLTEEMLKRLEEEKFQILD

RIRERTSKQNIPLTLSIGIGYKEDDLIQLADLAQSSLDLALGRGGDQVVI

KQPEGKVRFYGGKTNPMEKRTRVRARVISQALQELITQSDQVFVMGHRYP

DMDVIGSSLGVMRIAEMNDRNAYVVVEPGKMSPDVKRLMNEIEEYPNVIK

NIVTPQVALENITEKSLLVVVDTHKPSMVINKELLDSATNVVVVDHHRRS

EEFVGSPVLVYIEPYASSTAELITELFEYQPDLEQVGKIEATALLSGIVV

DTKNFTLRTGSRTFDAASYLRSLGADTILVQQFLKEDITTFTQRSRLVES

LEIYHDGMAIATGHEDEEFGTVIAAQAADTMLSMEGVQASFVITLRPDKL

IGISARSLGQINVQVIMEKLGGGGHLSNAATQLKDVTIAEAEKQLISAID

AYWKGET

The nucleic acid sequence of lmo0052 is:

(SEQ ID NO: 15)
ATGTCAGGCTATTTTCAAAAACGAATGCTTAAATATCCATTATACGGTCT

GATTGCAGCGACAATTATTTTGAGCGTAATCACGTTCTTTTTTCGTGGT

GGTTATCGGCGTTAGTTGTTGTTGGCGGAATTATTCTTACGGTTGCGATG

TTTTATTTTGAATATCGCTTGAATGAAGATGTGCAACTATATGTTTCTAA

TTTAACGTATCGGATTAAGCGTAGTGAAGAAGAAGCGCTTGTTGAAATGC

CGATGGGAATACTGCTGTATGATGAACATTACAAAATCGAATGGGTTAAC

CCGTTTATGTCAAAATACTTTGATAAGGCAGAGTTAATCGGGGAATCTTT

GGAAGAAGTAGGACCGGAATTTTTGGACGTTATTACTGGGAATGATGAAA

AGGGGATTATGTCGATTGCTTGGCGTGATCACCGTTTTGATACGATAGTA

AAGCGTAAGGAACGAATTTTATATTTATATGATCGCACAGAATATTATGA

TTTAAACAAGAAATTTCAAGCGAATAAATCTGTATTTGCGGTTATTTTCT

TAGATAATTATGATGAATGGGCGCAGGGCATGGATGATAGACGTCGCAGT

GCTTTAAATAATTTGGTGACGTCGATGTTGACCAACTGGGCTAGGGAACA

TCGTATTTATTTGAAACGGATTTCGACAGACCGATTTATGGCCTTTTTGA

CGGAGGAAATGTTGAAGCGGTTGGAGGAAGAGAAGTTTCAAATATTGGAC

CGGATTCGCGAACGGACGTCGAAGCAAAATATTCCTTTAACGCTTAGTAT

TGGGATTGGTTATAAGGAAGATGATTTGATTCAGCTGGCCGATTTGGCGC

AGTCTAGTCTAGATCTTGCTTTAGGGCGCGGCGGCGATCAGGTTGTAATT

AAGCAACCTGAAGGAAAAGTGCGTTTTTATGGTGGGAAAACAAATCCGAT

GGAAAAACGGACTCGTGTTCGCGCGCGTGTGATTTCGCAAGCATTGCAAG

AGCTGATTACGCAAAGTGACCAAGTTTTTGTTATGGGGCACCGCTATCCG

GATATGGACGTAATTGGTTCGAGTCTTGGAGTGATGCGGATTGCTGAGAT

GAATGATCGGAATGCTTATGTGGTTGTGGAACCTGGCAAAATGAGTCCAG

ATGTGAAGCGACTAATGAATGAAATTGAAGAATATCCGAATGTAATTAAA

AATATTGTTACACCGCAAGTCGCACTGGAAAATATCACGGAGAAGAGTTT

GCTCGTTGTTGTTGATACACACAAACCTTCGATGGTTATTAATAAGGAAT

TGCTGGACTCAGCTACGAATGTGGTTGTTGTCGATCATCACCGTCGTTCA

GAGGAATTTGTTGGGAGTCCGGTTCTTGTTTATATCGAGCCATATGCGTC

ATCTACTGCCGAATTGATTACGGAGCTATTTGAGTATCAACCGGATTTAG

AGCAGGTTGGGAAAATCGAGGCAACGGCGCTTCTTTCCGGGATTGTGGTT

GATACGAAGAACTTTACGCTGCGGACTGGGTCGCGAACGTTTGATGCGGC

AAGTTATTTACGGTCGCTTGGTGCGGACACGATTTTGGTGCAGCAATTTT

TGAAAGAAGATATTACTACTTTTACACAGCGGAGTCGTTTAGTGGAGTCG

CTTGAAATTTATCATGATGGTATGGCGATTGCGACTGGACATGAGGACGA

GGAATTTGGCACAGTTATAGCTGCGCAGGCGGCAGATACGATGCTTTCGA

TGGAAGGCGTGCAGGCATCCTTTGTTATTACGCTACGTCCGGATAAATTA

ATCGGGATTAGCGCGAGATCGCTTGGCCAAATCAATGTGCAAGTCATTAT

GGAAAAACTAGGCGGTGGCGGACATTTATCGAATGCAGCCACACAGCTTA

AAGATGTTACAATTGCAGAAGCAGAAAAACAATTAATTAGCGCCATTGAT

GCGTATTGGAAGGGAGAAACATAA

The lmo0052 mutant product may differ from the above sequence by 1 or more residues, where mutants of interest include deletion, insertion and substitution mutants.

Instead of or in addition to having enhanced secretion of c-di-AMP, mutant bacteria of interest also include bacteria that exhibit enhanced secretion of a di-adenylate cyclase and/or decreased secretion of a c-di-AMP phosphodiesterase. See, for example, U.S. Pat. No. 8,277,797, the disclosure of which is incorporated herein by reference. Accordingly, also of interest are Listeria bacteria wherein the mutation increases secretion of cytosolic di-adenylate cyclase, e.g., where the mutation increases the expression of multidrug efflux pumps (MDRs) in the bacteria, e.g. as described in the examples section below. Also of interest are Listeria bacteria comprising mutations that decrease secretion of c-di-AMP phosphodiesterase, e.g., bacteria that express transport-inactive MDR mutants, e.g. as described in the examples section below.

As mentioned above, mutant bacteria that result in decreased IFN production are also interest. Such bacteria may be employed for a number of different applications, including the delivery of vectors (e.g., viral vectors, plasmids, etc) or other material into the cytosol of a target cell. Bacteria of these embodiments may have reduced cyclase activity, e.g., they may include an lmo2120 nucleic acid mutation that results in expression of a product that has reduced activity as compared to wild type, or no activity, and or enhanced phosphodiesterase activity, e.g., they may overexpress lmo0052, or include an lmo0052 nucleic acid mutation that results in expression of a product that has greater activity as compared to wild type. For these applications, where desirable the bacteria may be strains that lyse in the cytosol, e.g., by expressing a phage holin and/or lysin.

The above-mutant bacteria may be fabricated using a variety of different protocols. As such, generation of the subject mutant bacteria may be accomplished in a number of ways that are well known to those of skill in the art, including deletion mutagenesis, insertion mutagenesis, and mutagenesis which results in the generation of frameshift mutations, mutations which effect premature termination of a protein, or mutation of regulatory sequences which affect gene expression. Where desired, expression may be mediated by a viral vector. Mutagenesis can be accomplished using recombinant DNA techniques or using traditional mutagenesis technology using mutagenic chemicals or radiation and subsequent selection of mutants. Representative protocols of different ways to generate mutant bacteria according to the present invention are provided in the Experimental Section, below.

In certain embodiments, the mutant *Listeria* bacteria are killed but metabolically active (KBMA). By the term "KBMA" or "killed but metabolically active" is meant that the bacteria are attenuated for entry into non-phagocytic cells and attenuated with respect to cell-to-cell spread resulting in bacteria that have greatly reduced toxicity and yet the immunogenicity of the bacteria is maintained. Such mutants include, but are not limited to, mutations in one or all uvr genes, i.e. uvrA, uvrB, uvrC, and uvrD genes as well as recA genes, or functionally equivalent genes, depending on the genus and species of the microbe. These mutations result in attenuation in the activity of the corresponding enzymes UvrA (an ATPase), UvrB (a helicase), UvrC (a nuclease), UvrD (a helicase II) and RecA (a recombinase). These mutants would typically be used in conjunction with a crosslinking compound, such as a psoralen. In one embodiment, there are attenuating mutations, such as deletions, in both uvrA and uvrB (uvrAB). KBMA mutations are further described in Brockstedt et al., Nature Med. 11, 853-860 (2005) and in U.S. Pat. No. 7,691,393.

In certain embodiments, the mutant *Listeria* bacteria are also attenuated. By the term "attenuation," as used herein, is meant a diminution in the ability of the bacterium to cause disease in an animal. In other words, the pathogenic characteristics of the attenuated *Listeria* strain have been lessened compared with wild-type *Listeria*, although the attenuated *Listeria* is capable of growth and maintenance in culture. Using as an example the intravenous inoculation of Balb/c mice with an attenuated *Listeria*, the lethal dose at which 50% of inoculated animals survive (LD50) is preferably increased above the LD50 of wild-type *Listeria* by at least about 10-fold, more preferably by at least about 100-fold, more preferably at least about 1,000 fold, even more preferably at least about 10,000 fold, and most preferably at least about 100,000-fold. An attenuated strain of *Listeria* is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

In certain embodiments, the attenuated mutant *Listeria* bacteria according to the subject invention are ones that exhibit a decreased virulence compared to their corresponding wild type strain in the Competitive Index Assay as described in Auerbach et al., "Development of a Competitive Index Assay To Evaluate the Virulence of *Listeria monocytogenes* actA Mutants during Primary and Secondary Infection of Mice," Infection and Immunity, September 2001, p. 5953-5957, Vol. 69, No. 9. In this assay, mice are inoculated with test and reference, e.g., wild-type, strains of bacteria. Following a period of time, e.g., 48 to 60 hours, the inoculated mice are sacrificed and one or more organs, e.g., liver, spleen, are evaluated for bacterial abundance. In these embodiments, a given bacterial strain is considered to be less virulent if its abundance in the spleen is at least about 50-fold, or more, such as 70-fold or more less than that observed with the corresponding wild-type strain, and/or its abundance in the liver is at least about 10-fold less, or more, such as 20-fold or more less than that observed with the corresponding wild-type strain. In yet other embodiments, bacteria are considered to be less virulent if they show abortive replication in less than about 8 hours, such as less than about 6 hours, including less than about 4 hours, as determined using the assay described in Jones and Portnoy, Intracellular growth of bacteria. (1994b) Methods Enzymol. 236:463-467. In yet other embodiments, bacteria are considered to be attenuated or less virulent if, compared to wild-type, they form smaller plaques in the plaque assay employed in the Experimental Section, below, where cells, such as murine L2 cells, are grown to confluency, e.g., in six-well tissue culture dishes, and then infected with bacteria. Subsequently, DME-agar containing gentamicin is added and plaques are grown for a period of time, e.g., 3 days. Living cells are then visualized by adding an additional DME-agar overlay, e.g., containing neutral red (GIBCO BRL) and incubated overnight. In such an assay, the magnitude in reduction in plaque size observed with the attenuated mutant as compared to the wild-type is, in certain embodiments, 10%, including 15%, such as 25% or more.

In certain embodiments, the subject bacteria are cytotoxic. A particular strain of bacteria is considered to be cytotoxic if it compromises its host cell in a period of less than about 8 hours, sometimes less than about 6 hours, e.g., in less than about 5 hours, less than about 4 hours, less than about 3 hours, less than about two hours, or less than about 1 hour, as determined using the cytotoxicity assay described below. In some instances, the strains may induce pyroptosis. Alternatively, or in addition, strains of the invention may be coadministered with other strains, e.g., strains that induce inflammasome activation.

In certain embodiments, mutant bacteria according to the subject invention express a heterologous antigen. The heterologous antigen is, in certain embodiments, one that is capable of providing protection in an animal against challenge by the infectious agent from which the heterologous antigen was derived, or which is capable of affecting tumor growth and metastasis in a manner which is of benefit to a host organism. Heterologous antigens which may be introduced into a *Listeria* strain of the subject invention by way of DNA encoding the same thus include any antigen which when expressed by *Listeria* serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor that expresses the said heterologous antigen(s). The host organism is preferably a mammal and most preferably, is a human.

By the term "heterologous antigen," as used herein, is meant a protein or peptide, a lipoprotein or lipopeptide, or any other macromolecule which is not normally expressed in *Listeria*, which substantially corresponds to the same antigen in an infectious agent, a tumor cell or a tumor-related protein. The heterologous antigen is expressed by a strain of *Listeria* according to the subject invention, and is processed and presented to cytotoxic T-cells upon infection of mammalian cells by the strain. The heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal. In other examples, the tumor cell antigen may be a mutant form of that which is naturally expressed in the mammal, and the antigen expressed by the *Listeria* species will conform to that tumor cell mutated antigen. By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens which may be introduced into *Listeria* by way of incorporating DNA encoding the same, include any known or heretofore unknown tumor antigen. In other examples, the "tumor-related antigen" has no effect on tumor growth or metastasis, but is used as a component of the *Listeria* vaccine because it is expressed specifically in the tissue (and tumor) from which the tumor is derived. In still other examples, the "tumor-related antigen" has no effect on tumor growth or metastasis, but is used as a component of the *Listeria* vaccine because it is selectively expressed in the tumor cell and not in any other normal tissues. The heterologous antigen useful in vaccine development may be selected using knowledge available to the skilled artisan, and many antigenic proteins which are expressed by tumor cells or which affect tumor growth or metastasis or which are expressed by infectious agents are currently known. For example, viral antigens which may be considered as useful as heterologous antigens include but are not limited to the nucleoprotein (NP) of influenza virus and the gag protein of HIV. Other heterologous antigens include, but are not limited to, HIV env protein or its component parts gp120 and gp41, HIV nef protein, and the HIV pol proteins, reverse transcriptase and protease. Still other heterologous antigens can be those related to hepatitis C virus (HCV), including but not limited to the E1 and E2 glycoproteins, as well as non-structural (NS) proteins, for example NS3. In addition, other viral antigens such as herpesvirus proteins may be useful. The heterologous antigens need not be limited to being of viral origin. Parasitic antigens, such as, for example, malarial antigens, are included, as are fungal antigens, bacterial antigens and tumor antigens.

As noted herein, a number of proteins expressed by tumor cells are also known and are of interest as heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer. Other coding sequences of interest include, but are not limited to, costimulatory molecules, immunoregulatory molecules, and the like.

The introduction of DNA encoding a heterologous antigen into a strain of *Listeria* may be accomplished, for example, by the creation of a recombinant *Listeria* in which DNA encoding the heterologous antigen is harbored on a vector, such as a plasmid for example, which plasmid is maintained and expressed in the *Listeria* species, and in whose antigen expression is under the control of prokaryotic promoter/regulatory sequences. Alternatively, DNA encoding the heterologous antigen may be stably integrated into the *Listeria* chromosome by employing, for example, transposon mutagenesis, homologous recombination, or integrase mediated site-specific integration (as described in U.S. Pat. No. 7,425,449, the disclosure of which is herein incorporated by reference).

Several approaches may be employed to express the heterologous antigen in *Listeria* species as will be understood by one skilled in the art once armed with the present disclosure. In certain embodiments, genes encoding heterologous antigens are designed to either facilitate secretion of the heterologous antigen from the bacterium or to facilitate expression of the heterologous antigen on the *Listeria* cell surface.

In certain embodiments, a fusion protein which includes the desired heterologous antigen and a secreted or cell surface protein of *Listeria* is employed. Listerial proteins which are suitable components of such fusion proteins include, but are not limited to, ActA, listeriolysin O (LLO) and phosphatidylinositol-specific phospholipase (PI-PLC). A fusion protein may be generated by ligating the genes which encode each of the components of the desired fusion protein, such that both genes are in frame with each other. Thus, expression of the ligated genes results in a protein comprising both the heterologous antigen and the Listerial protein. Expression of the ligated genes may be placed under the transcriptional control of a Listerial promoter/regulatory sequence such that expression of the gene is effected during growth and replication of the organism. Signal sequences for cell surface expression and/or secretion of the fused protein may also be added to genes encoding heterologous antigens in order to effect cell surface expression and/or secretion of the fused protein. When the heterologous antigen is used alone (i.e., in the absence of fused *Listeria* sequences), it may be advantageous to fuse thereto signal sequences for cell surface expression and/or secretion of the heterologous antigen. The procedures for accomplishing this are well know in the art of bacteriology and molecular biology.

The DNA encoding the heterologous antigen which is expressed is, in many embodiments, preceded by a suitable promoter to facilitate such expression. The appropriate promoter/regulatory and signal sequences to be used will depend on the type of Listerial protein desired in the fusion protein and will be readily apparent to those skilled in the art of *Listeria* molecular biology. For example, suitable *L. monocytogenes* promoter/regulatory and/or signal sequences which may be used to direct expression of a fusion protein include, but are not limited to, sequences derived from the *Listeria* hly gene which encodes LLO, the *Listeria* p60 (iap) gene, and the *Listeria* actA gene which encodes a surface protein necessary for *L. monocytogenes* actin assembly. Other promoter sequences of interest include the plcA gene which encodes PI-PLC, the *Listeria* mpl gene, which encodes a metalloprotease, and the *Listeria* inlA gene which encodes internalin, a *Listeria* membrane protein. The heterologous regulatory elements such as promoters derived from phage and promoters or signal sequences derived from other bacterial species may be employed for the expression of a heterologous antigen by the *Listeria* species.

In certain embodiments, the mutant *Listeria* include a vector. The vector may include DNA encoding a heterologous antigen. Typically, the vector is a plasmid that is capable of replication in *Listeria*. The vector may encode a heterologous antigen, wherein expression of the antigen is under the control of eukaryotic promoter/regulatory sequences, e.g., is present in an expression cassette. Typical plasmids having suitable promoters that are of interest include, but are not limited to, pCMV-β comprising the immediate early promoter/enhancer region of human cytomegalovirus, and those which include the SV40 early promoter region or the mouse mammary tumor virus LTR promoter region.

As such, in certain embodiments, the subject bacteria include at least one coding sequence for heterologous polypeptide/protein, as described above. In many embodiments, this coding sequence is part of an expression cassette, which provides for expression of the coding sequence in the *Listeria* cell for which the vector is designed. The term "expression cassette" as used herein refers to an expression module or expression construct made up of a recombinant DNA molecule containing at least one desired coding sequence and appropriate nucleic acid sequences necessary for the expression of the operably linked coding sequence in a particular host organism, i.e., the *Listeria* cell for which the vector is designed, such as the promoter/regulatory/signal sequences identified above, where the expression cassette may include coding sequences for two or more different polypeptides, or multiple copies of the same coding sequence, as desired. The size of the coding sequence and/or expression cassette that includes the same may vary, but typically falls within the range of about 25-30 to about 6000 bp, usually from about 50 to about 2000 bp. As such, the size of the encoded product may vary greatly, and a broad spectrum of different products may be encoded by the expression cassettes present in the vectors of this embodiment.

As indicated above, the vector may include at least one coding sequence, where in certain embodiments the vectors include two or more coding sequences, where the coding sequences may encode products that act concurrently to provide a desired results. In general, the coding sequence may encode any of a number of different products and may be of a variety of different sizes, where the above discussion merely provides representative coding sequences of interest.

c-di-AMP activity modulatory agents may also include nucleic acid/protein agents. For example, in addition to bacteria, e.g., as described above, c-di-AMP activity may be modulated by providing a desired di-adenylate cyclase activity and/or c-adenylate phosphodiesterase activity in the target cell. As such, a target cell may be contacted with an agent that modulates di-adenylate cyclase activity in the cell in a desired manner, e.g., an agent that increases di-adenylate cyclase activity in the cell. Examples of such agents include, but are not limited to, a polypeptide comprising a DAC domain, or a nucleic acid encoding a polypeptide comprising a DAC domain as described in greater detail above, e.g. a lmo2120 gene or DAC-active mutant thereof, or a DisA gene or DAC-active fragment thereof. which may be present in a vector and/or expression cassette, at desired. Alternatively or in addition, a target cell may be contacted with an agent that modulates c-di-AMP phosphodiesterase activity in a desired manner, e.g., an agent that decreases di-adenylate cyclase activity in the cell, such as a phosphodiesterase (PDE) inhibitor, a c-di-AMP phosphodiesterase-specific siRNA, etc.

In practicing methods according to embodiments of the invention, an effective amount of the active agent, i.e., a c-di-AMP activity modulatory agent (such as described above), is provided in the target cell or cells. As used herein "effective amount" or "efficacious amount" means the amount of an organism or compound that, when contacted with the cell, e.g., by being introduced into the cell in vitro, by being administered to a subject, etc., is sufficient to result in the desired c-di-AMP activity modulation. The "effective amount" will vary depending on cell and/or the organism and/or compound and or the nature of the desired outcome and/or the disease and its severity and the age, weight, etc., of the subject to be treated. In some instances, the effective amount of the modulatory agent is provided in the cell by contacting the cell with the modulatory agent. Contact of the cell with the modulatory agent may occur using any convenient protocol. The protocol may provide for in vitro or in vivo contact of the modulatory agent with the target cell, depending on the location of the target cell. For example, where the target cell is an isolated cell, e.g. a cell in vitro (i.e. in culture), or a cell ex vivo ("ex vivo" being cells or organs are modified outside of the body, where such cells or organs are typically returned to a living body), and the modulatory agent is an agent that modulates expression of a di-adenylate cyclase or phosphodiesterase, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the modulatory agent, and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995. As another example, where the target cell or cells are part of a multicellular organism, the modulatory agent may be administered to the organism or subject in a manner such that the agent is able to contact the target cell(s), e.g., via an in vivo protocol. By "in vivo," it is meant in the target construct is administered to a living body of an animal.

In some embodiments, the c-di-AMP activity modulatory agent is employed to modulate c-di-AMP activity in mitotic or post-mitotic cells in vitro or ex vivo, i.e., to produce modified cells that can be reintroduced into an individual. Mitotic and post-mitotic cells of interest in these embodiments include any eukaryotic cell, e.g. pluripotent stem cells, for example, ES cells, iPS cells, and embryonic germ cells; somatic cells, for example, hematopoietic cells, fibroblasts, neurons, muscle cells, bone cells, vascular endothelial cells, gut cells, and the like, and their lineage-restricted progenitors and precursors; and neoplastic, or cancer, cells, i.e. cells demonstrating one or more properties associated with cancer cells, e.g. hyperproliferation, contact inhibition, the ability to invade other tissue, etc. In certain embodiments, the eukaryotic cells are cancer cells. In certain embodiments, the eukaryotic cells are hematopoietic cells, e.g. macrophages, NK cells, etc. Cells may be from any mammalian species, e.g. murine, rodent, canine, feline, equine, bovine, ovine, primate, human, etc. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, blood cells, e.g. leukocytes, e.g. macrophages, may be harvested by apheresis, leukocytapheresis, density gradient separation, etc., while cells from tissues such as skin, muscle, bone marrow, spleen, liver, pancreas, lung, intestine, stomach, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

As mentioned above, the c-di-AMP activity modulatory agent may be provided to the cells as nucleic acids that encode for the c-di-AMP activity modulatory agent, e.g. a nucleic acid that encodes for a polypeptide comprising a DAC domain to increase di-AMP activity in the cell, or a nucleic acid that encodes for a phosphodiesterase to decrease di-AMP activity in the cell. mRNA encoding di-AMP activity modulatory agent(s) may be provided to the cells using well-developed transfection techniques; see, e.g. Angel and Yanik (2010) PLoS ONE 5(7): e11756, Beumer et al. (2008) PNAS 105(50):19821-19826, and the commercially available TransMessenger® reagents from Qiagen, Stemfect™ RNA Transfection Kit from Stemgent, and TransIT®-mRNA Transfection Kit from Mirus Bio LLC. Alternatively, nucleic acids encoding di-AMP activity modulatory agent(s) may be provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, AAV, etc.

Vectors may be provided directly to the subject cells. In other words, the cells are contacted with vectors comprising the nucleic acid encoding the c-di-AMP activity modulatory agent(s) such that the vectors are taken up by the cells. Methods for contacting cells with nucleic acid vectors that are plasmids, such as electroporation, calcium chloride transfection, and lipofection, are well known in the art. For viral vector delivery, the cells are contacted with viral particles comprising the nucleic acid encoding the c-di-AMP activity modulatory agent(s). Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing the nucleic acids encoding c-di-AMP activity modulatory agent(s) to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing c-di-AMP activity modulatory agent(s) to the subject cells may include nucleic acid sequences that encode for selectable markers in the target cells, so as to identify cells that have taken up the c-di-AMP activity modulatory agent(s).

c-di-AMP activity modulatory agent(s) may also be provided to cells as polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the c-di-AMP activity modulatory agent(s) may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO:016). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Pat. Nos. 7,256,286; 6,759,387; 7,585,834; and 7,229,961, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

The c-di-AMP activity modulatory agent(s) may be produced by eukaryotic cells or by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are c-di-AMP activity modulatory agent(s) polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The c-di-AMP activity modulatory agent(s) may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The c-di-AMP activity modulatory agent(s) may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

To modulate c-di-AMP activity, the c-di-AMP activity modulatory agent(s)—be they polypeptides or nucleic acids that encode c-di-AMP activity modulatory polypeptides—are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different c-di-AMP activity modulatory agents are provided to the cell, i.e. a c-di-AMP activity modulatory agent cocktail, the c-di-AMP activity modulatory agent(s) may be provided simultaneously, e.g. as two polypeptides delivered simultaneously, as two nucleic acid vectors delivered simultaneously, or as a single nucleic acid vector comprising the coding sequences for both fusion polypeptides. Alternatively, they may be provided consecutively, e.g. the first c-di-AMP activity modulatory agent being provided first, followed by the second c-di-AMP activity modulatory agent, etc. or vice versa.

Typically, an effective amount of c-di-AMP activity modulatory agent(s) are provided to the cells to induce a change in c-diAMP activity. An effective amount of c-di-AMP activity modulatory agent is the amount to induce a 2-fold increase or more in the amount of c-di-AMP activity observed relative to a negative control, e.g. a cell contacted with an empty vector or irrelevant polypeptide. That is to say, an effective amount or dose of c-di-AMP activity modulatory agent(s) will induce a 2-fold increase, a 3-fold increase, a 4-fold increase or more in the amount of c-di-AMP activity observed, in some instances a 5-fold increase, a 6-fold increase or more, sometimes a 7-fold or 8-fold increase or more in the amount of activity observed, e.g. an increase of 10-fold, 50-fold, or 100-fold or more, in some instances, an increase of 200-fold, 500-fold, 700-fold, or 1000-fold or more, in the amount of activity observed. The amount of activity may be measured by any convenient method. For example, the amount of interferon produced by the cell may be assessed after contact with the c-di-AMP activity modulatory agent(s), e.g. 2 hours, 4 hours, 8 hours, 12 hours, 24 hours, 36 hours, 48 hours, 72 hours or more after contact with the c-di-AMP activity modulatory agent (s).

Contacting the cells with the c-di-AMP activity modulatory agent(s) may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Following the methods described above, a cell may be modified ex vivo to have an increase in c-di-AMP activity. In some embodiments, it may be desirous to select for the modified cell, e.g. to create an enriched population of modified cells. Any convenient modification to the cells that marks the cells as modified with a c-di-AMP modulatory agent may be used. For example, a selectable marker may be inserted into the genome of the cell, so that the population of cells may be enriched for those comprising the genetic modification by separating the genetically marked cells from the remaining population. Separation may be by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the genetically modified cells.

Cell compositions that are highly enriched for cells comprising c-di-AMP activity modulatory agent(s) are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of cells comprising c-di-AMP activity modulatory agent(s).

Cells comprising c-di-AMP activity modulatory agent(s) produced by the methods described herein may be used immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The cells comprising c-di-AMP activity modulatory agent(s) may be cultured in vitro under various culture conditions. The cells may be expanded in culture, i.e. grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the regulatory T cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been modified with c-di-AMP activity modulatory agent(s) may be transplanted to a subject for purposes such as gene therapy, e.g. to treat a disease or as an antiviral, antipathogenic, or anticancer therapeutic, for the production of genetically modified organisms in agriculture, or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals, e.g. murine, lagomorpha, etc. may be used for experimental investigations.

Cells may be provided to the subject alone or with a suitable substrate or matrix, e.g. to support their growth and/or organization in the tissue to which they are being transplanted. Usually, at least $1\times10^3$ cells will be administered, for example $5\times10^3$ cells, $1\times10^4$ cells, $5\times10^4$ cells, $1\times10^5$ cells, $1\times10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g. U.S. Pat. No. 7,922,999, incorporated here by reference); or by implanting a device upon which the cells have been reversibly affixed (see e.g. U.S. Patent Application Publication No. 2008/0081064 A1 and U.S. Pat. No. 8,521,273, incorporated herein by reference).

The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In other aspects of the invention, the c-di-AMP activity modulatory agent(s) are employed to modify cellular c-di-AMP activity in vivo. In these in vivo embodiments, the c-di-AMP activity modulatory agent(s) are administered directly to the individual. c-di-AMP activity modulatory agent(s) may be administered by any of a number of well-known methods in the art for the administration of peptides, small molecules and nucleic acids to a subject. The c-di-AMP activity modulatory agent(s) can be incorporated into a variety of formulations. More particularly, the c-di-AMP activity modulatory agent(s) of the present invention can be formulated into pharmaceutical compositions by combination with appropriate pharmaceutically acceptable carriers or diluents.

In the subject methods, the active agent(s) may be administered to the targeted cells using any convenient administration protocol capable of resulting in the desired activity. Thus, the agent can be incorporated into a variety of formulations, e.g., pharmaceutically acceptable vehicles, for therapeutic administration. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Typically, an effective amount of c-di-AMP activity modulatory agent(s) are provided. As discussed above with regard to ex vivo methods, an effective amount or effective dose of a c-di-AMP activity modulatory agent in vivo is the amount to induce a 2 fold increase or more in the amount of c-di-AMP activity in the cell relative to a negative control, e.g. a cell contacted with an empty vector, irrelevant polypeptide, etc. The amount of activity may be measured by any convenient method, e.g. as described herein and known in the art. The calculation of the effective amount or effective dose of a c-di-AMP activity modulatory agent to be administered is within the skill of one of ordinary skill in the art, and will be routine to those persons skilled in the art. Needless to say, the final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the c-di-AMP activity modulatory agent(s) may be obtained from a suitable commercial source. As a general proposition, the total pharmaceutically effective amount of the c-di-AMP activity modulatory agent(s) administered parenterally per dose will be in a range that can be measured by a dose response curve.

c-di-AMP activity modulatory agent-based therapies, i.e. preparations of c-di-AMP activity modulatory agent(s) to be used for therapeutic administration, must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The c-di-AMP activity modulatory agent-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

As reviewed above, the subject methods result in the modulation of c-di-AMP activity inside a cell, where the target cell(s) may be in vitro or in vivo. In certain embodiments, the subject methods result in reduction in toxicity of a target gene, e.g., via a reduction in aggregation of a protein encoded thereby, in a target cell(s). In certain embodiments, the methods result in enhancement in function of a protein encoded by a target gene.

The above methods find use in a variety of different applications. Certain applications are now reviewed in the following Utility section.

Utility

The methods and compositions of the invention find use in a variety of applications, where such applications include modulation of interferon-8 production in a subject is desired. Specific applications of interest include those in which a subject is treated for a disease condition. In some embodiments, subjects suitable for treatment with a method of the present invention include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neurovascular glaucoma and Oster Webber syndrome, psoriasis, restenosis, fungal, parasitic and viral infections such cytomegaloviral infections. Subjects to be treated according to the methods of the invention include any individual having any of the above-mentioned disorders.

In other embodiments, subjects suitable for treatment with a method of the present invention include individuals who have been clinically diagnosed as infected with a hepatitis virus (e.g., HAV, HBV, HCV, delta, etc.), particularly HCV, are suitable for treatment with the methods of the instant invention. Individuals who are infected with HCV are identified as having HCV RNA in their blood, and/or having anti-HCV antibody in their serum. Such individuals include naïve individuals (e.g., individuals not previously treated for HCV, particularly those who have not previously received IFN-α-based or ribavirin-based therapy) and individuals who have failed prior treatment for HCV.

In other embodiments, subjects suitable for treatment with a method of the present invention include individuals having multiple sclerosis. Multiple sclerosis refers to an autoimmune neurodegenerative disease, which is marked by inflammation within the central nervous system with lymphocyte attack against myelin produced by oligodendrocytes, plaque formation and demyelization with destruction of the myelin sheath of axons in the brain and spinal cord, leading to significant neurological disability over time. Typically, at onset an otherwise healthy person presents with the acute or sub acute onset of neurological symptomatology (attack) manifested by unilateral loss of vision, vertigo, ataxia, dyscoordination, gait difficulties, sensory impairment characterized by paresthesia, dysesthesia, sensory loss, urinary disturbances until incontinence, diplopia, dysarthria or various degrees of motor weakness until paralysis. The symptoms are usually painless, remain for several days to a few weeks, and then partially or completely resolve. After a period of remission, a second attack will occur. During this period after the first attack, the patient is defined to suffer from probable MS. Probable MS patients may remain undiagnosed for years. When the second attack occurs the diagnosis of clinically definite MS (CDMS) is made (Poser criteria 1983; C. M. Poser et al., Ann. Neurol. 1983; 13, 227).

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms. As used herein, the term "treating" is thus used to refer to both prevention of disease, and treatment of pre-existing conditions. For example, where the mutant bacteria is administered, the prevention of cellular proliferation can be accomplished by administration of the subject compounds prior to development of overt disease, e.g. to prevent the regrowth of tumors, prevent metastatic growth, etc. Alternatively the compounds are used to treat ongoing disease, by stabilizing or improving the clinical symptoms of the patient.

Combination Therapy

For use in the subject methods, the c-di-AMP modulatory agents, such as the subject mutant *Listeria* described above, may be administered in combination with other pharmaceutically active agents, including other agents that treat the underlying condition or a symptom of the condition. In addition, the mutant *Listeria* may be used to provide an increase in the effectiveness of another chemical, such as a pharmaceutical, that is necessary to produce the desired biological effect.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Examples of other agents for use in combination therapy of neoplastic disease include, but are not limited to, thalidomide, marimastat, COL-3, BMS-275291, squalamine, 2-ME, SU6668, neovastat, Medi-522, EMD121974, CAI, celecoxib, interleukin-12, IM862, TNP470, avastin, gleevec, herceptin, and mixtures thereof. Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

Other antiviral agents can also be delivered in the treatment methods of the invention. For example, compounds that inhibit inosine monophosphate dehydrogenase (IMPDH) may have the potential to exert direct anti viral activity, and such compounds can be administered in combination with the mutant Listeria, as described herein. Drugs that are effective inhibitors of hepatitis C NS3 protease may be administered in combination with the mutant Listeria, as described herein. Hepatitis C NS3 protease inhibitors inhibit viral replication. Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein. Examples of other agents for use in combination therapy of multiple sclerosis include, but are not limited to; glatiramer; corticosteroids; muscle relaxants, such as Tizanidine (Zanaflex) and baclofen (Lioresal); medications to reduce fatigue, such as amantadine (Symmetrel) or modafinil (Provigil); and other medications that may also be used for depression, pain and bladder or bowel control problems that can be associated with MS.

In the context of a combination therapy, combination therapy compounds may be administered by the same route of administration (e.g. intrapulmonary, oral, enteral, etc.) that the mutant Listeria are administered. In the alternative, the compounds for use in combination therapy with the mutant Listeria may be administered by a different route of administration.

Adjuvant Compositions

The subject mutant bacterial strains, e.g., as described above, also find use as immunopotentiating agents, i.e., as adjuvants. In such applications, the subject attenuated bacteria may be administered in conjunction with an immunogen, e.g., a tumor antigen, modified tumor cell, etc., according to methods known in the art where live bacterial strains are employed as adjuvants. See, e.g., Berd et al., Vaccine 2001 Mar. 21; 19(17-19):2565-70.

In some embodiments, the mutant bacterial strains are employed as adjuvants by chemically coupling them to a sensitizing antigen. The sensitizing antigen can be any antigen of interest, where representative antigens of interest include, but are not limited to: viral agents, e.g., Herpes simplex virus; malaria parasite; bacteria, e.g., staphylococcus aureus bacteria, diphtheria toxoid, tetanus toxoid, shistosomula; tumor cells, e.g. CAD2 mammary adenocarcinomia tumor cells, and hormones such as thyroxine T4, triiodothyronine T3, and cortisol. The coupling of the sensitizing antigen to the immunopotentiating agent can be accomplished by means of various chemical agents having two reactive sites such as, for example, bisdiazobenzidine, glutaraldehyde, di-iodoacetate, and diisocyanates, e.g., m-xylenediisocyanate and toluene-2,4-diisocyanate. Use of Listeria spp. as adjuvants is further described in U.S. Pat. No. 4,816,253.

Vaccines

The subject bacteria, e.g., as described above, also find use as vaccines. The vaccines of the present invention are administered to a vertebrate by contacting the vertebrate with a sublethal dose of an attenuated mutant Listeria vaccine, where contact typically includes administering the vaccine to the host. In many embodiments, the attenuated bacteria are provided in a pharmaceutically acceptable formulation. Administration can be oral, parenteral, intranasal, intramuscular, intradermal, intraperitoneal, intravascular, subcutaneous, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and P. J. Weller, eds., Handbook of Pharmaceutical Excipients (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc. Immunizing a patient means providing the patient with at least some degree of therapeutic or prophylactic immunity against selected pathogens, cancerous cells, etc.

The subject vaccines find use in methods for eliciting or boosting a cellular immune response, e.g., a helper T cell or a cytotoxic T-cell response to a selected agent, e.g., pathogenic organism, tumor, etc., in a vertebrate, where such methods include administering an effective amount of the Listeria vaccine. The subject vaccines find use in methods for eliciting in a vertebrate an innate immune response that augments the antigen-specific immune response. Furthermore, the vaccines of the present invention may be used for treatment post-exposure or post diagnosis. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

In certain instances, the patient is one that has been predetermined, e.g., diagnosed, to be in need of type-I interferon production modulation. In some instances, the methods may include diagnosing the patient to be in need of type-I interferon production.

In general, the subject vaccines find use in vaccination applications as described U.S. Pat. Nos. 5,830,702 and 6,051,237, as well as PCT publication no WO 99/25376.

Kits

Kits with unit doses of the subject c-di-AMP activity modulatory agents, e.g., mutant Listeria, e.g., in oral or injectable doses, are provided. In the subject kits, the one or more components are present in the same or different containers, as may be convenient or desirable.

In addition to the containers containing the unit doses will be instructions describing the use and attendant benefits of the mutant Listeria in treating a pathological condition of interest. Instructions may be provided in a variety of different formats. In certain embodiments, the instructions may include complete protocols for practicing the subject methods or means for obtaining the same (e.g., a website URL directing the user to a webpage which provides the instructions), where these instructions may be printed on a substrate, where substrate may be one or more of: a package insert, the packaging, reagent containers and the like.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Overview

Listeria monocytogenes (Lm) is a gram-positive foodborn pathogen. Eradication of Lm infection relies on an adaptive cell-mediated immune response. This has led to the use of Lm as a vaccine platform, engineered to generate pathogen and tumor specific antigens that induce immunity toward a desired target. Such immunotherapies show particular promise for treatment of infectious and malignant disease. The success of genetically modified Lm as a vaccine is due to its ability to activate an innate immune response upon cytosolic entry, which is crucial to obtain optimal immunogenicity. Activation of a distinct host response upon cytosolic entry has led to the hypothesis of a cytosollic surveillance pathway (CSP), a branch of the innate immune system able to monitor the infiltration of the cytosol by microbes.[1] Here we identify cyclic di-adenosine monophosphate (c-di-AMP) as a CSP activating small molecule derived from Lm.

Here, we establish cytosolic sensing of c-di-AMP and show that this ligand contributes to type I interferon production during L. monocytogenes infection of macrophages. Given the importance of type-I interferon immunotherapy for malignant and chronic viral treatments and the promise of Lm as a vaccine platform, c-di-AMP, synthetic analogs, and Lm strains with variable production/secretion of c-di-AMP find use as adjuvant strains for vaccine development and IFN-β immunotherapeutics.

One major contribution of this work is the identification of type-I interferon induction by c-di-AMP. IFN-β immunotherapy shows promise in cancer drug regimens because of its anti-proliferative, anti-angiogenic, and immunomodulating effects on many human cancers. (Borden, E. C., J Interferon Cytokine Res 2005, 25, 511-527) However, IFN-β is limited by its short serum half-life. A small molecule, 5,6-dimethylxanthenone-4-acetic acid (DMXAA), currently in phase III clinical trials for cancer treatment, is therapeutically active due to its ability to stimulate IFN-β production. Given the small, drug-like nature of c-di-AMP, this molecule or synthetic analogs thereof are useful as IFN-β inducing therapeutics, much like DMXAA. Furthermore, Lm strains that have increased levels of c-di-AMP secretion also find use as type-I IFN inducing therapeutics.

Another contribution of this work is the establishment of cytosolic sensing of the c-di-AMP. One significant advantage of using Lm as a delivery platform for c-di-AMP is that it allows the molecule to gain access to the cytosol, where the host detects it. Given that c-di-AMP is not cell permeable and does not induce inflammation when added to the outside of cells, this method will offer significant advantage over using the purified molecule as an adjuvant or IFN inducing agent, where cytosolic delivery is difficult to attain.

Two families of proteins have recently been described, the di-adenylate cyclase domain (DAC, previously DUF147) that catalyzes the formation of c-di-AMP, and the DHH/DHHA1 domain that is a c-di-AMP phosphodiesterase (Rao, F. et al. J Biol Chem 2009; Witte, G et al. Mol Cell 2008, 30, 167-178). Listeria has one known di-adenylate cyclase, lmo2120, and one known c-di-AMP phosphodiesterase, lmo0052. Deletion or overexpression of each of these proteins or heterologous proteins with similar activity in Lm results in altered levels of c-di-AMP production and IFN production during host infection. These proteins can either be expressed in the bacterium to alter secretion levels of c-di-AMP or secreted to alter the extracellular concentration of the nucleotide. For instance, secretion of the protein lmo2120 into the cytosol of the host where ample levels of ATP, the substrate for the DAC, are present leads to the generation of c-di-AMP directly in the cytosol to enhance IFN production from the infected cell. Conversely, secretion of the c-di-AMP specific phosphodiesterase destroys secreted c-di-AMP and results in lower levels of IFN produced during infection. Such strains that generate altered levels of c-di-AMP may be rationally designed as vaccine platforms and immunotherapeutics for treatment of chronic and malignant disease.

II. Cyclic di-AMP Secreted by *Listeria monocytogenes* MDRs Activates a Host Cytosolic Surveillance Pathway

A. Introduction

Intracellular pathogens, such as *Listeria monocytogenes*, are detected in the cytosol of host immune cells, although the activating ligand(s) are not known. Induction of this host response is often dependent on microbial secretion systems, and in *L. monocytogenes*, it is dependent on multidrug efflux pumps (MDRs) of the MFS family. Using *L. monocytogenes* mutants that over-express MDRs, we identified cyclic diadenosine monophosphate (c-di-AMP) as a secreted molecule able to activate the cytosolic host response. Over-expression of the di-adenylate cyclase, dacA (lmo2120), resulted in elevated levels of the host response during infection. These studies identify a small molecule (c-di-AMP), predicted to be present in a wide variety of bacteria and archea, that triggers a cytosolic pathway of innate immunity, and are consistent with this nucleotide being secreted by bacterial MDRs.

Intracellular pathogens, such as *Listeria monocytogenes*, are detected in the cytosol of host immune cells leading to transcription of type I interferon and co-regulated genes. Although the activating ligand(s) are unknown, induction of this host response is often dependent on microbial secretion systems, and in *L. monocytogenes*, it is dependent on multidrug efflux pumps (MDRs) of the MFS family. Using *L. monocytogenes* mutants that over-express MDRs, we identified cyclic diadenosine monophosphate (c-di-AMP) as a secreted molecule able to activate the cytosolic host response. Over-expression of the di-adenylate cyclase, dacA (lmo2120), resulted in elevated levels of the host response during infection. These studies identify a small signalling molecule (c-di-AMP), predicted to be present in a wide variety of bacteria and archea, that triggers a cytosolic pathway of innate immunity.

B. Results

The mammalian innate immune system is comprised of receptors that collectively serve as a pathogen sensor to monitor the extracellular, vacuolar and cytosolic cellular compartments.[1] Recognition of microbes within these distinct compartments leads to cellular responses that are commensurate with the microbial threat. While both pathogenic and non-pathogenic microbes interact with extracellular and vacuolar compartments, infectious disease agents often mediate their pathogenesis by delivery of virulence factors directly into the host cell cytosolic compartment. Thus, an attractive hypothesis has emerged that the innate immune system distinguishes between pathogenic and non-pathogenic microbes by monitoring the sanctity of the cytosol.[2, 3]

Several distinct pathways of innate immunity are present in the host cell cytosol. One, termed the cytosolic surveillance pathway (CSP), detects bacterial, viral and protozoan pathogens, leading to the activation of IRF3 and NF-κB and induction of IFN-β and co-regulated genes.[4] Some ligands that activate this pathway are known, for example, viral nucleic acids. However, the ligands and host receptors that lead to IFN-β by non-viral microbes, including *L. monocy-togenes, M. tuberculosis, F. tularensis, L. pneumophila, B. abortis*, and *T. cruzi*, among others, remain unknown.[4-9]

In a previous study, we used a genetic screen to search for microbial factors that affect this host innate immune pathway.[10] We found that expression of *L. monocytogenes* multidrug efflux pumps (MDRs) of the major facilitator superfamily controlled the capacity of cytosolic bacteria to induce host expression of IFN-β. Ectopic expression of multiple MDRs led to enhanced IFN-β production, while one, MdrM, controlled the majority of the response to wild-type bacteria.

Figure 5:
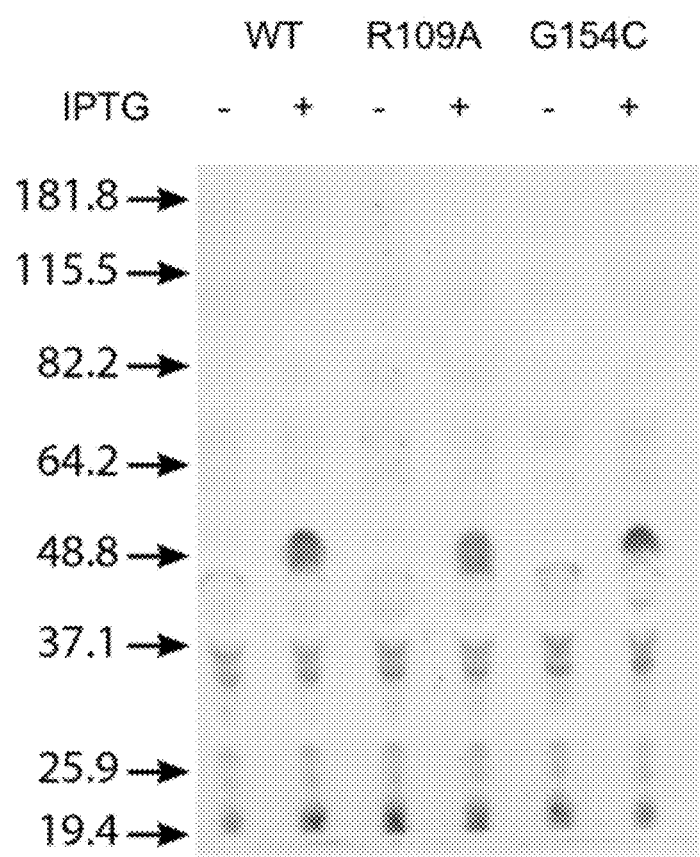
FIG. 5. Western blot of membrane fraction from the mdrM-*L. monocytogenes* strain integrated with an IPTG inducible plasmid containing WT, R109A, and G154C variants of hexa-histidine tagged MdrM. A total of 75 μg of membrane protein were separated by SDS-PAGE gel electrophoresis and blotted onto PVDF membrane. Blots were probed with a primary anti-histidine antibody and a secondary antibody conjugated to an infrared emitting fluorophore (Licor). Blots were imaged using the Odyssey Infrared Imaging System. The IPTG inducible, anti-His(6x) cross-reactive band at 48.8 kDa was quantified using the accompanying software.

Given that MDRs are known to transport small molecules (<1000 Da), we hypothesized that *L. monocytogenes* secretes a bioactive small molecule that is recognized within the host cytosol. However, over-expression of bacterial MDRs may compromise membrane integrity and increase delivery of microbial ligands non-specifically. Non-specific delivery of bacterial ligand(s) during infection would, therefore, be independent of transport activity of MDRs but dependent on transporter expression. To address these two possibilities, *L. monocytogenes* strains that over-express transport inactive mutants of MdrM were generated. Hexahistidine tagged, site-directed mutants (R109A and G154C) and WT MdrM under control of IPTG induction were introduced into the mdrM-*L. monocytogenes* strain. These two specific residues are conserved in MFS family MDRs and are crucial to transport activity.[11-13] Comparable membrane incorporation of wild-type and mutant variants of MdrM and similar intracellular growth of each strain was observed by western-blot of membrane fractions (FIG. 5 for representative blot) and infection of bone marrow derived macrophages, respectively (FIG. 1*a*-*b*). Only the WT, transport-competent expressing strain activated the CSP (FIG. 1*c*). These results are consistent with the need for transport activity of MDRs to induce IFN-β expression during infection and secretion of an active small molecule by these transporters.

Figure 2:
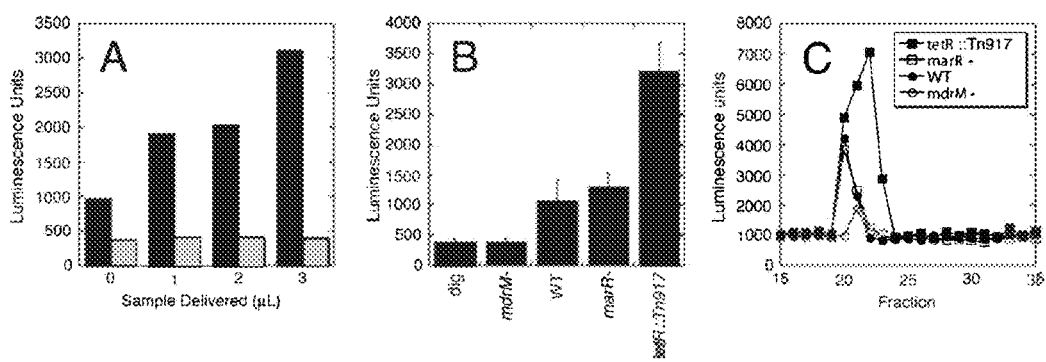
FIG. 2. (A) IFN-β production by BMMs in response to solid phase extracts (SPE) of marR-*L. monocytogenes* supernatants in the presence (black bars) and absence (grey bars) of digitonin. IFN-β activity was measured using ISRE L929 cells that generate luciferase in response to type-I IFN stimulation. Data are mean of biological replicates (N=2). (B) IFN-β activity by BMMs in response to solid phase extracts of sterile filtered culture supernatants from mdrM-, wild-type (WT), marR-, and tetR::Tn917 strains of *L. monocytogenes*. Negative control consists of digitonin permeabilizing solution alone (dig). Data are mean±SD (N=2). Data representative of two independent experiments. (C) IFN-β stimulatory activity of culture supernatants fractionated using reversed-phase HPLC. Activity measured as in (A). Data are the mean activity of biological replicates (N=2)

To identify the bioactive ligand(s) secreted by *L. monocytogenes* MDRs, we performed solid phase extraction (SPE) of the culture supernatant from an MdrM overexpressing *L. monocytogenes* strain (marR-, DP-L5445) that exhibits an IFN-β hyper-activating phenotype. Delivery of the fraction to the macrophage cytosol using reversible digitonin permeabilization[14] resulted in a dose-dependent increase in type-I IFN (FIG. 2*a*). Addition of this fraction in the absence of digitonin resulted in no IFN production, consistent with cytosolic detection of the active ligand.

Previous characterization of *L. monocytogenes* strains that exhibit variable levels of MDR expression demonstrated that IFN-β production correlates with increases in transporter levels.[10] Here, supernatants from four *L. monocytogenes* strains, mdrM-, WT, marR-, and tetR::Tn917, that exhibit increasing levels of MDR expression, respectively, were tested for activity. Comparable to infection assays, MDR expression correlated with IFN inducing activity of the culture supernatants (FIG. 2*b*), where the tetR::Tn917 strain exhibited significantly higher activity than any other strain, while the mdrM-strain lacked detectable activity above background.

Figure 6:
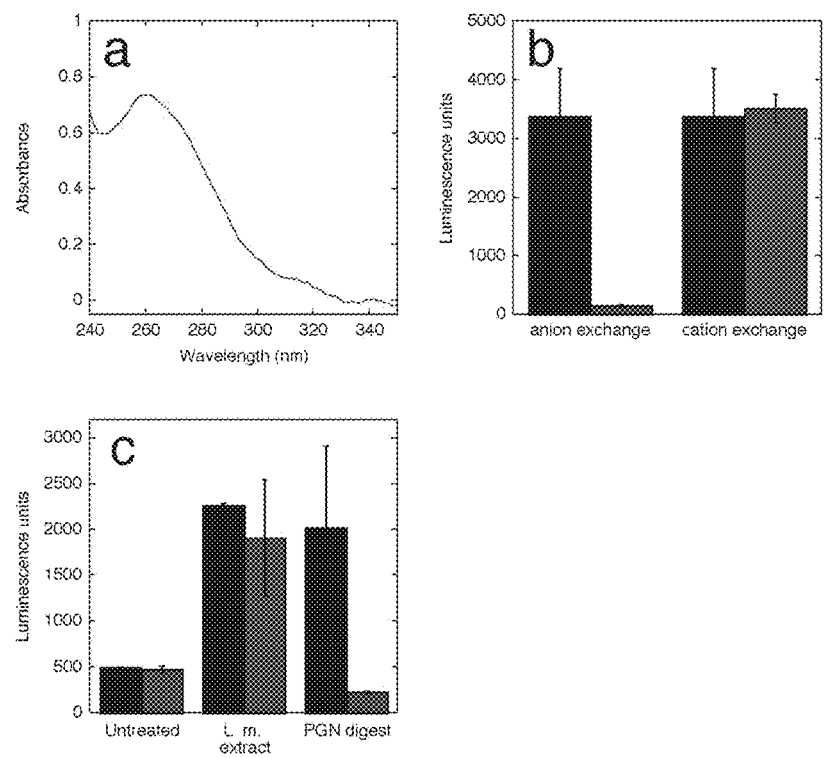
FIG. 6. (a) Absorbance spectrum from tetR::Tn917 *L. monocytogenes* HPLC fraction 22 ($\lambda_{max}$=260 nm). (b) Active fraction from marR-*L. monocytogenes* were mixed with (grey bars) and without (black bars) anion and cation exchange resins. Resin was removed by centrifugation and the supernatant was tested for IFN-β stimulatory activity with BMMs and ISRE cells. (c) Digested cell wall from *L. monocytogenes* in the presence (grey bars) and absence (black bars) of DNAse (PGN digest) was delivered to macrophage cytosol using lipofectamine 2000. Solid phase extract from marR-*L. monocytogenes* (L.m. extract) was treated similarly and IFN-β stimulatory activity was measured as in FIG. 1a. Error bars represent standard deviations of single samples measured in triplicate.

Fractionation of the active samples obtained from each MDR strain was performed using reversed-phase high performance liquid chromatography (RP-HPLC). The active component of each supernatant eluted as a single peak from the column with similar retention time (FIG. 2*c*), consistent with each containing the same active ligand. Furthermore, the magnitude of the active peak correlated with MDR expression. The sample with the highest activity exhibited a significant absorbance at 260 nm (FIG. 6*a*). Incubation with anion but not cation exchange resin removed the active molecule from solution (FIG. 6b), although treatment of the active sample was resistant to DNAse (FIG. 6c). These results were consistent with a non-DNA, nucleic acid as the active component.

Figure 7:
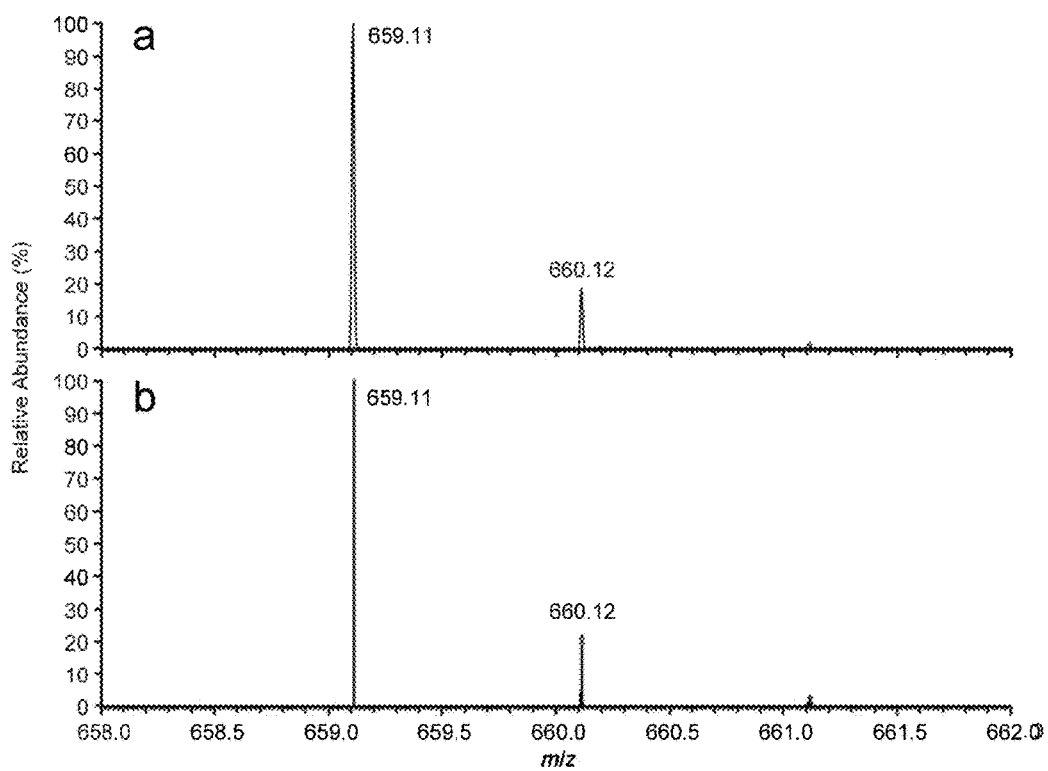
FIG. 7. Identification of c-di-AMP from *Listeria monocytogenes*. (a) Isotopically resolved electrospray ionization mass spectrum measured in the positive ion mode for a fraction of *Listeria monocytogenes*, showing detail for the range m/z=658-662. (b) Isotopic distribution calculated for the (M+H)$^+$ ion of c-di-AMP (M=$C_{20}H_{24}N_{10}O_{12}P_2$). The simulated spectrum of (b) was calculated from the natural abundances of the isotopes using Xcalibur software (version 4.1, Thermo).
Figure 8:
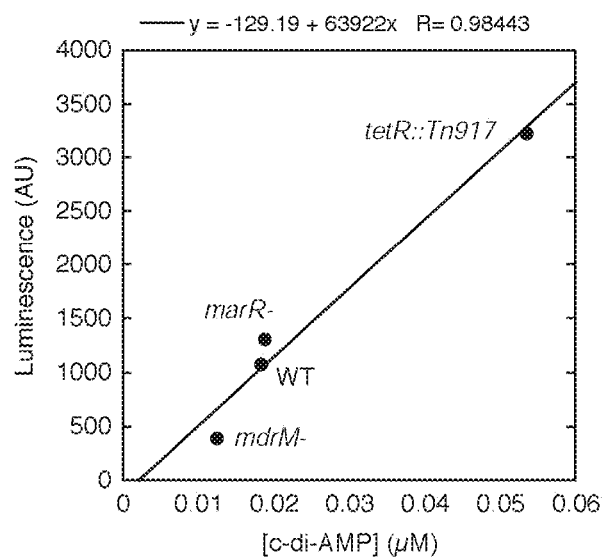
FIG. 8. Correlation between IFN-β inducing activity of *L. monocytogenes* supernatants and [c-di-AMP] in these supernatants, as measured by mass spectroscopy. IFN-β induction was measured using an interferon bioassay with ISRE L929 cells. Concentration of c-di-AMP was determined by mass spectrometry in comparison with a synthetic standard of known concentration. Line represents linear regression fit to data. Equation of fit above the graph.

To identify the IFN-β inducing metabolite contained in the fractions, samples were analyzed by high-resolution mass spectrometry. A single ion (m/z=659.11, z=1) was identified as exclusively present in the active fractions and absent in the inactive samples (FIG. 7a). The parent ion mass were consistent with cyclic di-adenosine monophosphate (c-di-AMP, FIG. 7b). Collision induced dissociation was performed to further characterize the identified ion (FIG. 3a). Comparison of the fragmentation pattern with synthetic standard (BioLog Life Science Institute, Denmark) confirmed the assignment of the ion (FIGS. 3b-c). Quantification of c-di-AMP in these samples revealed that the mdrM-, WT, and marR-strains had 23%, 34%, and 35% as much c-di-AMP in the culture supernatants relative to tetR:: Tn917 (53 nM), respectively. These results established that IFN-β inducing activity of L. monocytogenes supernatants correlates linearly with c-di-AMP concentration (FIG. 8).

Figure 4:
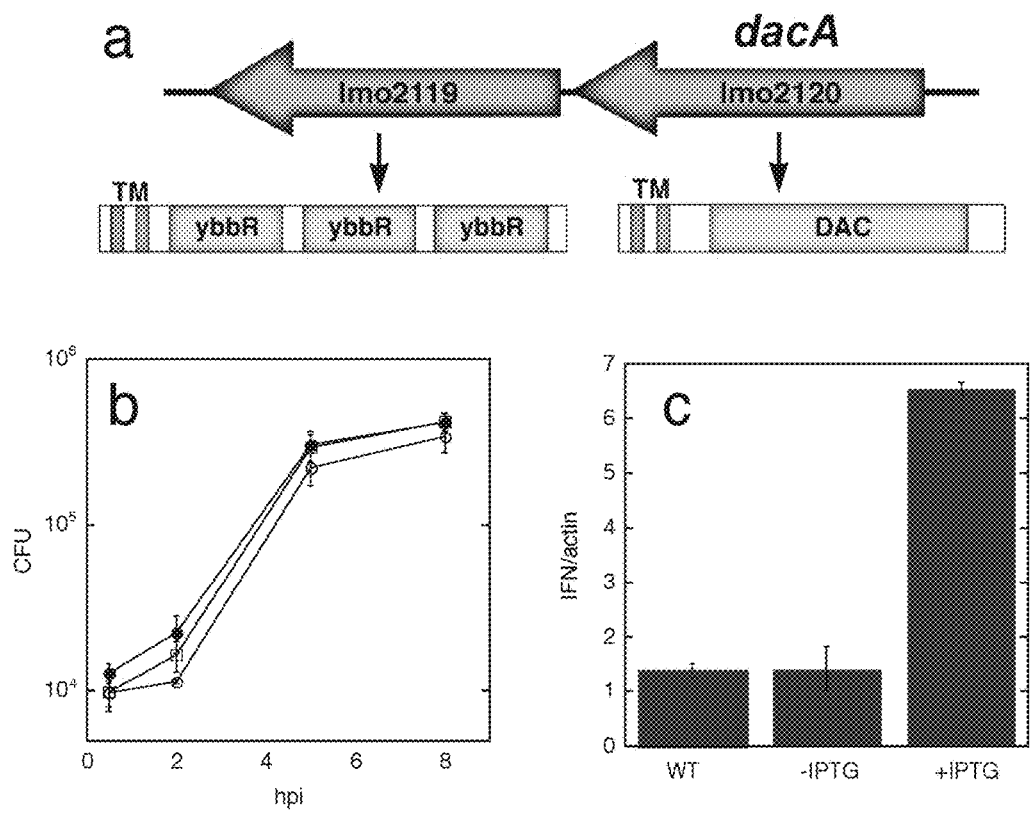
FIG. 4. The di-adenylate cyclase gene dacA (lmo2120) alters CSP activation during infection. (a) Predicted operon of genes lmo2120, renamed here dacA, and lmo2119. The product of each gene is predicted to contain two transmembrane spanning segments (TM). The gene product of lmo2119 contains three ybbR domains of unknown function. The gene product of lmo2120 contains a single di-adenylate cyclase (DAC) domain. (b) Intracellular growth curves of WT *L. monocytogenes* (closed circles) and *L. monocytogenes* with an integration vector (pLIV2) containing IPTG inducible dacA in the absence (open circles) and presence (open squares) of IPTG (1 mM) in BMMs. (c) qRT-PCR analysis of IFN-β induction by each strain in BMMs.
Figure 9:
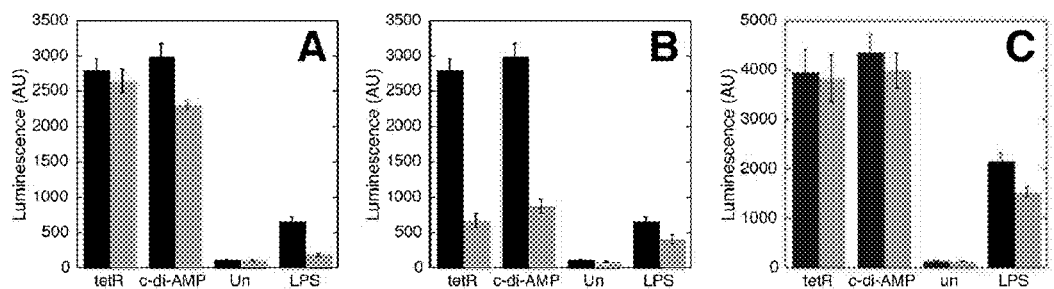
FIG. 9. Cytosolic detection of *L. monocytogenes* vs. c-di-AMP. Type-I interferon was measured in response to the tetR::Tn917 strain of *L. monocytogenes*, c-di-AMP, and LPS in (A) WT (black bars) and myd88-trif−/− (grey bars), (B) WT (black bars) and irf3−/− (grey bars), and (C) mays+/−(black bars) and mays−/− (grey bars) macrophages. *L. monocytogenes* infection was performed at an MOI of 4. Digitonin was used to deliver c-di-AMP to the cytosol. LPS was used as a positive control. Type-I IFN was measured using the ISRE L929 cells from supernatants of BMMs after 6 hours.

Next, we tested the ability of commercially available c-di-AMP to induce IFN-β in macrophages. Similar to the active sample, c-di-AMP exhibits a dose-dependent response when delivered to the cytosol of murine BMMs (FIG. 3d). Treatment of the purified active fraction and the commercial standard with snake venom phosphodiesterase (SVPD) abolished the activity of each sample. The host pathway responsible for cytosolic detection of L. monocytogenes is dependent on IRF3 and STING but independent of MyD88/Trif and MAVS.[10, 15] Detection of c-di-AMP requires a parallel host-signaling pathway, consistent with c-di-AMP as the relevant ligand of L. monocytogenes (FIG. 9). The above results demonstrate that the intracellular pathogen L. monocytogenes generates the novel nucleotide, c-di-AMP, which induces the host cytosolic surveillance pathway. This is the first evidence of c-di-AMP production and secretion in live bacteria and is the second report of the production of this novel di-nucleotide. A single other report assigned di-adenylate cyclase (DAC) activity to a domain of unknown function (previously DUF147) within the protein DisA of B. subtilis.[16] Based on these observations and previous reports pertaining to DisA, it was hypothesized that c-di-AMP acts a secondary signaling molecule that regulates bacterial sporulation. Bio-informatic analysis showed the widespread presence of the DAC domain in bacteria and archeae, including pathogenic Staphylococci, Streptococci, Mycobacteria, Chlamydia, and Mycoplasma spp.[17] Analysis of the genome of L. monocytogenes revealed a single gene, lmo2120, containing a predicted DAC domain. This gene is present in an operon with the downstream gene lmo2119, a gene of unknown function (FIG. 4a). Attempts to delete the gene lmo2120 using standard techniques were unsuccessful. Genes containing DAC domains in Streptococci and two species of Mycoplasma have been identified as essential,[18-20] supporting a similar indispensable role in L. monocytogenes. However, over-expression of lmo2120 did not affect bacterial growth but did lead to increased CSP activation during macrophage infection FIGS. 4b-c). These results are consistent with DAC activity encoded by the lmo2120 gene, which we have named here dacA.

A transposon insertion in L. monocytogenes lmo0052 was identified in a forward genetic screen for mutants that affect host cell death and IFN-β production (Sauer, J. D., et al. (2010). Cell Host Microbe 7, 412). Disruption of lmo0052 resulted in elevated levels of IFN-β compared to infection with wild-type L. monocytogenes. Sequence analysis identified Lmo0052 as a homolog of B. subtilis YybT, which was recently shown to have c-di-AMP phosphodiesterase activity (Rao, F., et al. (2010). J Biol Chem 285, 473). Lmo0052, renamed here PdeA, has 50% identity and 74% similarity to YybT and shares the multi-domain structure of YybT with two N-terminal transmembrane domains, a PAS signaling domain, a modified GGDEF domain, and C-terminal DHH and DHH-associated domains. Purified PdeA catalyzed conversion of c-di-AMP to the linear dinucleotide pApA, and purification of truncated constructs showed this activity was localized to the DHH/DHHA1 domains, thereby confirming previous biochemical characterization of homologous proteins (Rao et al., supra). Together these data suggest that PdeA is a c-di-AMP phosphodiesterase.

To define how each of these proteins affects c-di-AMP, we constructed a clean deletion of pdeA and over-expressed the gene. To achieve high levels of over-expression, pdeA was placed downstream of $P_{actA}$ in the PrfA*G145S background strain, where the promoter is constitutively active at high levels (Ripio, M. T., et al. (1997). J Bacteriol 179, 1533). As discussed above, we also manipulated expression of DacA. To do this, we introduced of a second copy of the dacA gene using an IPTG-inducible integration vector, pLIV2 (Fischetti, V. A. (2006). "Gram-Positive Pathogens", ASM Press, Washington, D.C.). In this genetic background, successful deletion of the chromosomal dacA was accomplished in the presence of inducer (cΔdacA). Removal of IPTG from these cultures resulted in a conditional dacA mutant (Li, Z., et al. (2005). Infect Immun 73, 5065).

Multiple attempts to measure intracellular levels of c-di-AMP were unsuccessful. To define how expression of these proteins affects c-di-AMP metabolism, c-di-AMP secretion by each strain was measured in chemically defined minimal media. As discussed above, ectopic over-expression of bacterial MDRs or DacA resulted in increased levels of c-di-AMP in the culture supernatant. Both the conditional deletion of dacA and over-expression of pdeA were predicted to lead to depletion of c-di-AMP. Indeed, lower levels of c-di-AMP were observed in culture supernatants of these strains, although it should be noted that cΔdacA mutant reached 50% of the levels of growth of other strains in minimal media. The clean deletion of pdeA was predicted to result in high levels of intracellular c-di-AMP, as has been shown in B. subtilis and Staphylococcus aureus mutants deficient in PdeA homologs (Corrigan, R. M., et al. (2011). PLoS Pathog 7, e1002217; Oppenheimer-Shaanan, Y., et al. (2011). EMBO Rep 12, 594). Surprisingly, PdeA-deficiency did not significantly affect levels secreted into the supernatant during broth culture even though increased IFN-β was observed during infection.

As discussed above and in Sauer et al. 2011 (Sauer, J D et al. (2011). Infect Immun 79, 688) c-di-AMP secreted by L. monocytogenes during infection leads to Type 1 interferon production. Although pdeA-deficient mutants are predicted to contain high levels of intra-bacterial c-di-AMP, we observed that the amount secreted by these mutants into the culture supernatant was comparable to levels observed with wild-type L. monocytogenes. To address this paradox, we infected murine bone marrow-derived macrophages and quantified induction of IFN-β by qRT-PCR. PdeA-deficient mutants stimulated nearly 5-fold more IFN-β than wild-type L. monocytogenes, indicating that more c-di-AMP is secreted in the host cell cytosol. This intracellular-specific release of c-di-AMP suggests that some condition within the host cell may trigger c-di-AMP secretion during infection and is physiologically distinct from the signal that leads to secretion during in vitro broth growth.

C. Discussion

Active secretion of a specific cyclic di-nucleotide by *L. monocytogenes* MDR transporters is an unprecedented observation with two important implications. First, MDRs are generally recognized to function in conferring resistance to small toxic molecules by active efflux, preventing accumulation of lethal concentrations within the cell. A number of instances have described transport of small molecules that are not toxic,[21-23] leading to the hypothesis that these transporters have evolved to transport specific natural substrates as well.[24] The observations presented show that these proteins play a broader biological role beyond general drug resistance, including bacterial signaling. Second, bacterial signaling nucleotides are generally considered to act within the cell. Here, we show that this molecule may be exported from the cell. These observations show that c-di-AMP is involved in extracellular signaling by *L. monocytogenes*.

Sensing of conserved and essential microbial molecules by the host is an evolutionary adaptation that maximizes microbial detection with a limited number of germ-line encoded receptors. Given the widespread presence of the DAC domain and the important role it plays in bacterial growth, this bacterial specific nucleotide is an attractive innate immune ligand. A number of reports demonstrate that microbe specific nucleotides induce inflammation in the host and, due to immunomodulatory effects, enhance protection to bacterial infection.[25-28] Furthermore, c-di-GMP specifically activates the host IFN pathway when delivered to the host cytosol.[29] Given the widespread appearance of the DAC domain in bacteria, it is likely that c-di-AMP is involved in pathogen recognition beyond *L. monocytogenes*, and, together with c-di-GMP, represent a class of ligands responsible for cytosolic activation of IFN-β by bacteria.

C. References

1. Ishii, K. J.; Koyama, S.; Nakagawa, A.; Coban, C.; Akira, S., *Cell Host Microbe* 2008, 3, 352-363.
2. Vance, R. E.; Isberg, R. R.; Portnoy, D. A., *Cell Host Microbe* 2009, 6, 10-21.
3. Lamkanfi, M.; Dixit, V. M., *Immunol Rev* 2009, 227, 95-105.
4. O'Riordan, M.; Yi, C. H.; Gonzales, R.; Lee, K. D.; Portnoy, D. A., *Proc Natl Acad Sci USA* 2002, 99, 13861-13866.
5. Henry, T.; Brotcke, A.; Weiss, D. S.; Thompson, L. J.; Monack, D. M., *J Exp Med* 2007, 204, 987-994.
6. Roux, C. M.; Rolan, H. G.; Santos, R. L.; Beremand, P. D.; Thomas, T. L.; Adams, L. G.; Tsolis, R. M., *Cell Microbiol* 2007, 9, 1851-1869.
7. Stetson, D. B.; Medzhitov, R., *Immunity* 2006, 24, 93-103.
8. Stanley, S. A.; Johndrow, J. E.; Manzanillo, P.; Cox, J. S., *J Immunol* 2007, 178, 3143-3152.
9. Vaena de Avalos, S.; Blader, I. J.; Fisher, M.; Boothroyd, J. C.; Burleigh, B. A., *J Biol Chem* 2002, 277, 639-644.
10. Crimmins, G. T.; Herskovits, A. A.; Rehder, K.; Sivick, K. E.; Lauer, P.; Dubensky, T. W., Jr.; Portnoy, D. A., *Proc Natl Acad Sci USA* 2008, 105, 10191-10196.
11. Paulsen, I. T.; Brown, M. H.; Skurray, R. A., *Microbiol Rev* 1996, 60, 575-608.
12. Kimura, T.; Nakatani, M.; Kawabe, T.; Yamaguchi, A., *Biochemistry* 1998, 37, 5475-5480.
13. De Jesus, M.; Jin, J.; Guffanti, A. A.; Krulwich, T. A., *Biochemistry* 2005, 44, 12896-12904.
14. Girardin, S. E.; Boneca, I. G.; Carneiro, L. A.; Antignac, A.; Jehanno, M.; Viala, J.; Tedin, K.; Taha, M. K.; Labigne, A.; Zahringer, U.; Coyle, A. J.; DiStefano, P. S.; Bertin, J.; Sansonetti, P. J.; Philpott, D. J., *Science* 2003, 300, 1584-1587.
15. Ishikawa, H.; Ma, Z.; Barber, G. N., *Nature* 2009, 461, 788-792.
16. Witte, G.; Hartung, S.; Buttner, K.; Hopfner, K. P., *Mol Cell* 2008, 30, 167-178.
17. Romling, U., *Sci Signal* 2008, 1, pe39.
18. French, C. T.; Lao, P.; Loraine, A. E.; Matthews, B. T.; Yu, H.; Dybvig, K., *Mol Microbiol* 2008, 69, 67-76.
19. Song, J. H.; Ko, K. S.; Lee, J. Y.; Baek, J. Y.; Oh, W. S.; Yoon, H. S.; Jeong, J. Y.; Chun, J., *Mol Cells* 2005, 19, 365-374.
20. Glass, J. I.; Assad-Garcia, N.; Alperovich, N.; Yooseph, S.; Lewis, M. R.; Maruf, M.; Hutchison, C. A., 3rd; Smith, H. O.; Venter, J. C., *Proc Natl Acad* Sci USA 2006, 103, 425-430.
21. Woolridge, D. P.; Vazquez-Laslop, N.; Markham, P. N.; Chevalier, M. S.; Gerner, E. W.; Neyfakh, A. A., *J Biol Chem* 1997, 272, 8864-8866.
22. van Helvoort, A.; Smith, A. J.; Sprong, H.; Fritzsche, I.; Schinkel, A. H.; Borst, P.; van Meer, G., *Cell* 1996, 87, 507-517.
23. Yang, S.; Lopez, C. R.; Zechiedrich, E. L., *Proc Natl Acad Sci USA* 2006, 103, 2386-2391.
24. Neyfakh, A. A., *Trends Microbiol* 1997, 5, 309-313.
25. Ebensen, T.; Schulze, K.; Riese, P.; Link, C.; Morr, M.; Guzman, C. A., *Vaccine* 2007, 25, 1464-1469.
26. Brouillette, E.; Hyodo, M.; Hayakawa, Y.; Karaolis, D. K.; Malouin, F., *Antimicrob Agents Chemother* 2005, 49, 3109-3113.
27. Karaolis, D. K.; Means, T. K.; Yang, D.; Takahashi, M.; Yoshimura, T.; Muraille, E.; Philpott, D.; Schroeder, J. T.; Hyodo, M.; Hayakawa, Y.; Talbot, B. G.; Brouillette, E.; Malouin, F., *J Immunol* 2007, 178, 2171-2181.
28. Karaolis, D. K.; Newstead, M. W.; Zeng, X.; Hyodo, M.; Hayakawa, Y.; Bhan, U.; Liang, H.; Standiford, T. J., *Infect Immun* 2007, 75, 4942-4950.
29. McWhirter, S. M.; Barbalat, R.; Monroe, K. M.; Fontana, M. F.; Hyodo, M.; Joncker, N. T.; Ishii, K. J.; Akira, S.; Colonna, M.; Chen, Z. J.; Fitzgerald, K. A.; Hayakawa, Y.; Vance, R. E., *J Exp Med* 2009, 206, 1899-1911.

D. Materials and Methods

1. Site Directed Mutants of MdrM

The open reading frame of MdrM was amplified from *L. monocytogenes* strain 10403S genomic DNA and the stop codon was removed using the following primers: 3'-GAG GAG CAT ATG AAT ATG AAA GCA GCA AGT ACA TCA G-5' (SEQ ID NO:01) and 3'-GAG GAG CTC GAG TGC TTT TTC CGT TTT AGT AAC AAT TG-5' (SEQ ID NO:02). The resulting fragment was digested with NdeI and XhoI and ligated into similarily digested pET20b. The resulting open reading frame, containing a hexa-histidine tag, was subsequently amplified using the following primers: 3'-GAGGAG CGG CCG ATG AAT ATG AAA GCA GCA AGT ACA TC-5' (SEQ ID NO:03) and 3'-GAGGAG GTC GAC TCA GTG GTG GTG GTG GTG G-5' (SEQ ID NO:04). The amplification product was digested using EagI and SalI and ligated into similarily digested pLIV2 to generate the IPTG inducible construct pLIV2:MdrMHis6×. The R109A MdrM DNA construct was made using quick change mutagenesis with the following primers: 5'-CCA TGC TGA TTG CTG GGG CAA TGG TAC AAG CAA TTG G-3' (SEQ ID NO:05) and 5'-CCA ATT GCT TGT ACC ATT GCC CCA GCA ATC AGC ATG G-3 (SEQ ID NO:06)' with pLIV2:MdrMHis6× as the template DNA. The G154C MdrM DNA construct was made using quick change mutagenesis with the following primers: 5'-GAA CTT TGC CCC AGC AAT TTG CCC GAC ACT TTC AGG-3'(SEQ ID NO:07) and 5'-CCT GAA AGT GTC GGG CAA ATT GCT GGG GCA AAG TTC-3' (SEQ ID NO:08) with pLIV2: MdrMHis6× as the template DNA. DNA sequencing was performed by the UC Berkeley DNA sequencing. Mutant plasmid was transformed into chemically Z-competent (Zymo Research) SM10 *E. coli* cells and conjugated with the mdrM-*L. monocytogenes* strain.

2. Intracellular Growth Curves

Bacterial growth in bone marrow derived macrophages was performed as described previously (S1). Briefly, BMMs (3×106 cells/dish) were plated in a monolayer on 12×1 mm round cover slips in 60 mm round petri dishes the night before infection. Bacteria were grown overnight at 30° C. in BHI. When appropriate, bacteria were grown overnight with IPTG (1 mM). In the morning bacteria were pelleted by centrifugation and washed 3 times with PBS. Macrophages were infected with 2×105 bacteria. Infections were washed 3× with PBS at 30 minutes post infections and gentamycin (50 μg/mL) was added at 1 hour post infection. Cover slips were removed and placed into sterile MQ water to lyse macrophages. Various dilutions were plated to determine the number of colony forming units.

3. DacA Inducible *L. monocytogenes* Strain

An IPTG inducible plasmid containing the open reading frame (ORF) of dacA (Imo2120) was integrated into the *L. monocytogenes* chromosome. The ORF of dacA was amplified using the following primers: 5'-GAG GAG CGG CCG ATG GAT TTT TCC AAT ATG TCG ATA TTG-3' (SEQ ID NO:09) and 5'-GAG GAG GTC GAC ATT TAA AAT TCG ATC CAT CAT TCG CT-3' (SEQ ID NO:10). The PCR amplification product was then digested with EagI and SalI and ligated with similarly digest pLIV2 plasmid. The plasmid was then conjugated into *L. monocytogenes* using *E. coli* SM10. DNA sequencing was performed by the UC Berkeley DNA sequencing.

4. Fractionation of *L. monocytogenes* Culture Supernatants

Various strains of *L. monocytogenes* were cultured overnight shaking at 37° C. in brain heart infusion (BHI) media. The following morning, overnight cultures were used to inoculate 50 mL of BHI media (OD600=0.02), which were subsequently grown with shaking at 37° C. until OD600=0.5. Cells were then pelleted by centrifugation and resuspended in 50 mL of chemically defined minimal media (S2). Cultures were grown at 37° C., shaking for 19 hours followed by centrifugation to remove bacteria. The supernatant was subsequently filtered through 0.4 μm nitrocellulose membrane filter (Millipore) and the pH of the supernatants was adjusted to 4.0 with concentrated HCl. Supernatants were then applied to Sep-Pak columns (Waters Corp., 6 cc, 500 mg C18) by gravity. The column was subsequently washed in succession with 5 mL each of 0.1% (w/v) trichloroacetic acid (TCA), 50% MeOH mixed with 0.1% TCA, and MeOH. Each wash was collected as a separate fraction and dried using a SpeedVac concentrator. The resulting pellet was resuspended in 1 mL of water and assayed for IFN-β stimulatory activity. Active fractions were further fractionated using reversed-phase high performance liquid chromatography (RP-HPLC) on an Agilent 1100 LC system. A fraction of the active sample (100 μL) was loaded onto a Waters Nova-Pak C18 column (4 μm, 3.9×150 mm) equilibrated with 0.1% formic acid (Solvent A). The column was developed at 0.5 mL/minute with an initial 5 minute wash with 100% Solvent A, a gradient of 0-50% MeOH over 40 minutes, a gradient from 50-100% MeOH over 5 minutes, followed by 100% MeOH for 3 minutes and a return to 100% water. Fractions (0.5 mL) were collected over the entire run. Each fraction was dried using a SpeedVac, resuspended in 50 μL of water, and tested for IFN-β stimulating activity in bone marrow derived macrophages.

5. Purification and Digestion of *L. monocytogenes* Peptidoglycan

*L. monocytogenes* grown overnight in BHI was used to inoculate 1 L culture of BHI to an optical density of 0.02. Cells grown at 37° C. with shaking to an optical density of 1 were harvested by centrifugation. Bacteria were resuspended in PBS with 5% SDS and boiled for 30 minutes. Cells were separated by centrifugation and then washed 2 times with water and then run through a French press 3 times at 14000 psi. Cells then were resuspended in PBS and bead beat for 10 minutes and subsequently separated by centrifugation. Pellets from centrifugation were resuspended in 4% boiling SDS for 30 minutes. Sample was cooled and cell wall was pelleted by centrifugation. Supernatant was removed and pellet resuspended in 4% SDS and boiled for 15 minutes. Cell wall was then washed with hot water, 0.1% Triton, and five more times with hot water. Finally, purified cell wall was resuspended in mutanolysin buffer (50 mM MES pH 5.9, 1 mM $MgCl_2$). Cell wall (15 mg) was digested with mutanolysin (50 units, Sigma Aldrich, *Streptomyces globisporus*) in the presence and absence of DNAse (5 Kunitz units, Qiagen). IFN-β inducing activity of these samples was assessed using the IFN-β bioassay. Attempts to use digitonin delivery with DNA were unsuccessful with either double stranded DNA oligonucleotides or digested bacterial cell wall. As such, delivery of samples to the macrophage cytosol was performed using Lipofectamine 2000 (Invitrogen) according to the manufacturer's protocol.

6. Ion Exchange Pull-Down

To characterize the charge of the active component secreted by *L. monocytogenes*, active fractions from HPLC purification of the marRsupernatant were incubated with cation-exchange resin (SP650M, Toyopearl) or anionexchange resin (Q650M, Toyopear) for 30 minutes with agitation at room temperature. Resin was removed by centrifugation and the activity remaining in the supernatant was measure by IFN-β bio-assay.

7. IFN-β Bio-Assay

Mouse bone marrow from 6-8 week old female mice was differentiated to bone marrow derived macrophages (BMM) as described previously (S3). Interferon responsive ISRE-L929 cells were cultured in ISRE media (DMEM, 2 mM glutamine, 1 mM pyruvate, 10% heat inactivated FBS, and penicillin-streptomycin). Induction of type-I interferon was assessed using BMMs plated in 96-well flat bottom tissue culture treated plates (105 cells/well) a minimum of 12 hours prior to use in BMM media (DMEM, 2 mM glutamine, 1 mM pyruvate, 10% CSF from 3T3 cells, and 20% heat inactivated FBS). Samples (10 µL) of *L. monocytogenes* supernatants, HPLC fractions, and cyclic di-AMP standard (Biolog Life Sciences Institute, Denmark) were mixed with a 10× volume of digitonin permeabilization solution (50 mM HEPES pH 7.0, 100 mM KCl, 3 mM MgCl2, 0.1 mM DTT, 85 mM Sucrose, 0.2% BSA, 1 mM ATP, 0.1 mM GTP, ±10 µg/mL Digitonin) (S4). Media was aspirated from the cells and replaced with 50 µL each sample mixture. Cells were incubated for 30 minutes at 37° C. Wells were again aspirated and fresh BMDM media (50 µL/well) was added. At 4 hours post initial addition of sample, supernatants were removed and applied in various dilutions to the interferon responsive ISRE-L929 cells (5×104 cells/well) in white, 96-well, tissueculture treated plates (Thermo Scientific Nunc). Cells were incubated for 4 hours, media aspirated, and 40 µL of TNT lysis buffer (20 mM Tris, 100 mM NaCl, 1% triton, pH 8.0) was added to each well. Finally, 40 µL of luciferase substrate solution (20 mM Tricine, 2.67 mM $MgSO_4 \cdot 7H_2O$, 0.1 mM EDTA, 33.3 mM DTT, 530 µM ATP, 270 µM acetyl CoA lithium salt, 470 µM luciferin, 5 mM NaOH, 265 µM magnesium carbonate hydroxide) was added to each well and luminescence was measured using a VICTOR3 luminometer (PerkinElmer).

8. Liquid Chromatography Mass Spectrometry (LC-MS) Analysis

*Listeria monocytogenes* fractions were analyzed using an Agilent 1200 series liquidchromatograph (LC; Santa Clara, Calif.) connected in-line with an LTQ Orbitrap XL hybrid mass spectrometer equipped with an Ion Max electrospray ionization source (ESI; Thermo Fisher Scientific, Waltham, Mass.). Acetonitrile (Fisher Optima grade, 99.9%) and formic acid (Pierce, 1 mL ampules, 99+%) purchased from Fisher Scientific (Pittsburgh, Pa.), and water purified to a resistivity of 18.2 MΩ·cm (at 25° C.) using a Milli-Q Gradient ultrapure water purification system (Millipore, Billerica, Mass.), were used to prepare mobile phase solvents for liquid chromatography. The LC was equipped with C8 guard (Poroshell 300SB-C8, 5 µm, 12.5×2.1 mm, Agilent) and analytical (75×0.5 mm) columns. Solvent A was 0.1% formic acid/99.9% water and solvent B was 0.1% formic acid/99.9% acetonitrile (v/v). Sample solutions contained in 0.3 mL polypropylene snap-top vials sealed with rubber septa caps (Wheaton Science, Millville, N.J.) were loaded into the Agilent 1200 autosampler compartment prior to analysis. A 50 µL injection volume was used for each sample.

Following sample injection, analyte trapping was performed for 5 min with 99.5% A at a flow rate of 90 µL/min. The elution program consisted of a linear gradient from 5% to 95% B over 27 min, isocratic conditions at 95% B for 10 min, a linear gradient to 0.5% B over 1 min, and then isocratic conditions at 0.5% B for 16 min, at a flow rate of 90 µL/min. The column and sample compartment were maintained at 35° C. and 10° C., respectively. Solvent (Milli-Q water) blanks were run between samples, and the autosampler injection needle was rinsed with Milli-Q water after each sample injection, to avoid cross-contamination between samples. The connections between the LC column exit and the ESI probe of the mass spectrometer were made using PEEK tubing (0.005" i.d.×1/16" o.d., Western Analytical, Lake Elsinore, Calif.). External mass calibration was performed prior to analysis using the standard LTQ calibration mixture containing caffeine, the peptide MRFA, and Ultramark 1621 dissolved in 51% acetonitrile/25% methanol/23% water/1% acetic acid solution (v/v). The ESI source parameters were as follows: ion transfer capillary temperature 275° C., normalized sheath gas (nitrogen) flow rate 25%, ESI voltage 2.0 kV, ion transfer capillary voltage 49 V, and tube lens voltage 120 V. Full scan mass spectra were recorded in the positive ion mode over the range m/z=100 to 1500 using the Orbitrap mass analyzer, in profile format, with a full MS automatic gain control target setting of 5×105 charges and a resolution setting of 6×104 (at m/z=400, FWHM). In the data-dependent mode, the most intense ion measured from each full scan mass spectrum exceeding an intensity threshold of 15,000 counts was selected for tandem mass spectrometry (MS/MS) analysis. MS/MS spectra were acquired using the Orbitrap mass analyzer, in profile format, with a resolution setting of 1.5×104 (at m/z=400, FWHM), using collisionally activated dissociation (CAD) with an isolation width of 2 m/z units, a normalized collision energy of 28%, and a default charge state of 1+. To avoid the occurrence of redundant MS/MS measurements, real-time dynamic exclusion was enabled to preclude re-selection of previously analyzed precursor ions using a repeat count of one, a repeat duration of 5 s, a maximum exclusion list size of 100 different precursor ions, an exclusion duration of 180 s, and an exclusion width of 1.5 m/z units.

Mass spectra and MS/MS spectra were processed using Xcalibur software (version 4.1, Thermo). ChemBioDraw Ultra software (version 11.0.1, CambridgeSoft, Cambridge, Mass.) was used to draw and calculate the exact masses of candidate chemical structures for comparison with measured masses. To quantify c-di-AMP in *L. monocytogenes* supernatants, the four fractions eluted from HPLC purification of the nucleotide surrounding the peak of activity were pooled for each strain and analyzed by LC-MS. The observed peak for ion 659.11 m/z was integrated using Xcalibur software. The concentration of the nucleotide was determined by comparing the integrated peak area to a calibration curve generated using synthetic c-di-AMP samples of known concentration analyzed in a similar way.

9. IFN-β Induction in Various Host Strains

BMMs were differentiated as described previously (S3). For mays−/− macrophages, heterozygous mice were used as a control. WT and mutant BMMs were plated in 24-well plates (5×106 cells/well) the evening prior to use. For infections, 2×106 bacteria from 30° C. overnight cultures were washed with PBS and added to each well containing 500 µL of BMM media. For c-di-AMP treatment, synthetic standard was dissolved in digitonin solution to a final concentration of 3 µM. Media was aspirated from cells and replaced with 200 µL of c-di-AMP/digitonin mix. From this point on infections and c-di-AMP samples were treated the same. At 30 minutes wells were aspirated and replaced with fresh BMM media. At 1 hour post infection gentamycin (50 µg/mL) was added. For LPS treatment, 100 ng of sonicated LPS stock solution (50 µg/mL) was added to appropriate wells containing 500 µL of BMM media. Supernatants from all wells were collected and analyzed by ISRE L929 bioassay for IFN-β activity at 6 hours.

10. Supporting References

S1. D. A. Portnoy, P. S. Jacks, D. J. Hinrichs, Role of hemolysin for the intracellular growth of *Listeria monocytogenes*. J. Exp. Med. 167, 1459 (1988).

S2. L. Phan-Thanh, T. Gormon, A chemically defined minimal medium for the optimal culture of *Listeria. Int. J. Food Microbiol.* 35, 91 (1997).

S3. J. H. Leber et al., Distinct TLR- and NLR-mediated transcriptional responses to an intracellular pathogen. *PLoS Pathog.* 4, e6 (2008).

S4. S. E. Girardin et al., Nod1 detects a unique muropeptide from gram-negative bacterial peptidoglycan. *Science* 300, 1584 (2003).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

That which is claimed is:

1. A method of enhancing type-I interferon production in a eukaryotic cell, the method comprising:
increasing cytosolic cyclic di-adenosine monophosphate (c-di-AMP) activity in the eukaryotic cell in a manner sufficient to modulate type-I interferon production in the cell, wherein the method comprises enhancing cytosolic di-adenylate cyclase activity in the cell.

2. The method according to claim 1, wherein the method further comprises introducing c-di-AMP or a functional analogue thereof into the cell.

3. The method according to claim 1, wherein the method comprises overexpressing a polypeptide having di-adenylate cyclase activity.

4. A method of enhancing type-I interferon production in a eukaryotic cell comprising cytosolic cyclic di-adenosine monophosphate (c-di-AMP), the method comprising:
increasing cytosolic c-di-AMP activity in the eukaryotic cell in a manner sufficient to modulate type-I interferon production in the cell, wherein the method comprises decreasing activity of a c-di-AMP phosphodiesterase in the cell.

5. The method according to claim 4, wherein the method comprises contacting the cell with an inhibitor of c-di-AMP phosphodiesterase.

6. A method of decreasing type-I interferon production in a eukaryotic cell comprising cytosolic cyclic di-adenosine monophosphate (c-di-AMP), the method comprising:
decreasing cytosolic c-di-AMP activity in the cell by decreasing production of c-di-AMP in the cytosol, enhancing destruction of c-di-AMP in the cytosol, inhibiting the activity of c-di-AMP in the cytosol, or a combination thereof.

7. The method according to claim 6, wherein the method comprises introducing a c-di-AMP activity inhibitor into the cell.

8. The method according to claim 6, wherein the method comprises contacting the cell with an agent that decreases activity of a cytosolic di-adenylate cyclase in the cell.

9. The method according to claim 8, wherein the agent is a di-adenylate cyclase-specific siRNA.

10. The method according to claim 6, wherein the method comprises increasing c-di-AMP phosphodiesterase activity in the cell.

11. The method according to claim 10, wherein the method comprises overexpressing a c-di-AMP phosphodiesterase in the cell.

12. The method according to claim 1, wherein the cell is a macrophage.

13. The method according to claim 1, wherein the type-I interferon is interferon-β.

14. The method according to claim 1, wherein the cell is in vitro.

15. The method according to claim 1, wherein the cell is part of a multi-cellular organism.

16. The method according to claim 15, wherein the multi-cellular organism is a mammal.

17. The method according to claim 16, wherein the method further comprises expressing a heterologous protein in a subject.

18. The method according to claim 16, wherein the method is a method of treating said mammal for a disease condition.

19. The method according to claim 4, wherein the method comprises introducing c-di-AMP or a functional analogue thereof into the cell.

20. The method according to claim 6, wherein the eukaryotic cell comprises a bacterium that secretes c-di-AMP, a di-adenylate cyclase or both in the cytosol.

\* \* \* \* \*